(12) United States Patent
Tanabe et al.

(10) Patent No.: US 10,876,106 B2
(45) Date of Patent: Dec. 29, 2020

(54) GENE ANALYSIS SYSTEM

(71) Applicant: Hitachi, Ltd., Tokyo (JP)

(72) Inventors: Maiko Tanabe, Tokyo (JP); Masataka Shirai, Tokyo (JP); Tomoyuki Sakai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 85 days.

(21) Appl. No.: 15/553,175

(22) PCT Filed: Apr. 9, 2015

(86) PCT No.: PCT/JP2015/061077
§ 371 (c)(1),
(2) Date: Aug. 24, 2017

(87) PCT Pub. No.: WO2016/162997
PCT Pub. Date: Oct. 13, 2016

(65) Prior Publication Data
US 2018/0119135 A1    May 3, 2018

(51) Int. Cl.
| C07H 21/04 | (2006.01) |
| C12M 1/34 | (2006.01) |
| C12M 1/00 | (2006.01) |
| C12Q 1/68 | (2018.01) |
| C12N 15/10 | (2006.01) |
| C12Q 1/6886 | (2018.01) |

(52) U.S. Cl.
CPC .......... *C12N 15/1065* (2013.01); *C12M 1/00* (2013.01); *C12N 15/1096* (2013.01); *C12Q 1/68* (2013.01); *C12Q 1/6886* (2013.01); *C12Q 2600/158* (2013.01)

(58) Field of Classification Search
None
See application file for complete search history.

(56) References Cited

U.S. PATENT DOCUMENTS

| 2007/0026439 A1* | 2/2007 | Faulstich ............ B01F 13/0059 435/6.14 |
| 2012/0245053 A1 | 9/2012 | Shirai et al. |
| 2014/0066318 A1 | 3/2014 | Frisen et al. |
| 2014/0378317 A1 | 12/2014 | Fu et al. |
| 2015/0167063 A1 | 6/2015 | Shirai et al. |

FOREIGN PATENT DOCUMENTS

| JP | 2009284834 | 12/2009 |
| WO | 2003035841 | 5/2003 |
| WO | 2011068088 | 6/2011 |
| WO | 2014020657 | 2/2014 |

OTHER PUBLICATIONS

Shirai et al, WO2014020657 A1, Machine english translation of WO2014/020657 A1, pp. 1-24, 2014.*
International Search Report of PCT/JP2015/061077 dated Jul. 14, 2015.
Luo Yacui, et al, "ICP-MS-Based Multiplex and Ultrasensitive Assay of Viruses with Lanthanide-Coded Biospecific Tagging and Amplification Strategies", Anal. Chem., 2013, vol. 85, No. 20, pp. 9428-9432.

* cited by examiner

*Primary Examiner* — Sarae L Bausch
(74) *Attorney, Agent, or Firm* — Mattingly & Malur, PC

(57) ABSTRACT

In order to interpret an arbitrary sequence region in many genes in many cells, it is necessary to degrade a nucleic acid into fragments and introduce a sequence that is different from one cell to another into each of the fragments. However, in the conventional configuration for analyzing many cells, there has been a problem that mixing of the degraded fragments among areas occurs before a tag sequence unique for each of the areas is introduced. The present invention provides a system for capturing a nucleic acid extracted from a cell in each of plural areas on a substrate and synthesizing a complementary DNA (cDNA) of the nucleic acid for each of the areas, wherein the system also includes a means for immediately introducing a tag sequence unique for each of the areas to the reaction product.

16 Claims, 12 Drawing Sheets

Specification includes a Sequence Listing.

(a)

(b)

(c)

(d)

(e)

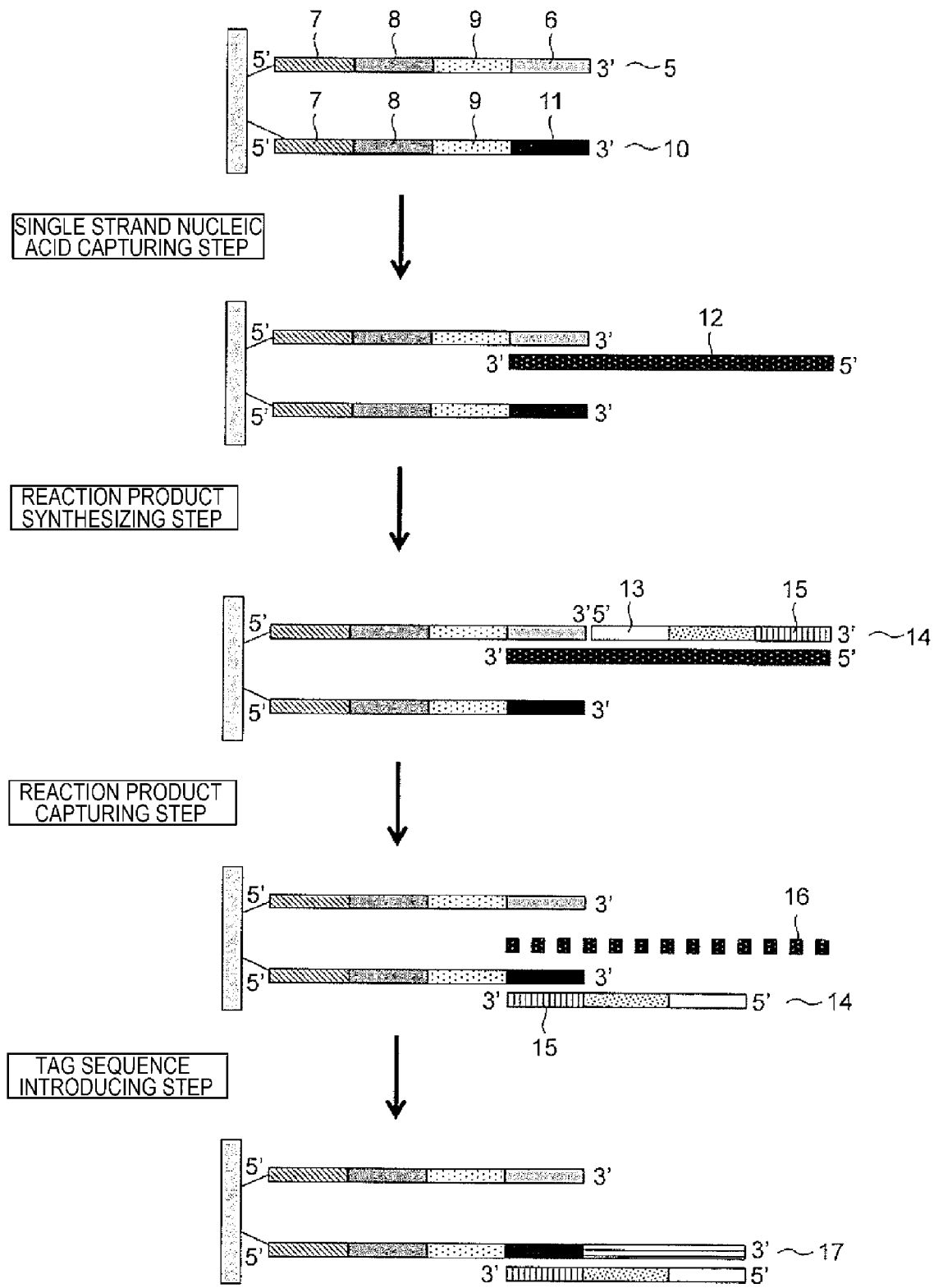

(a)

(b)

(c)

(a)

(b)

(c)

SEQUENCE LISTING

```
<160> NUMBER OF SEQ ID NOS: 9

<210> SEQ ID NO 1
<211> LENGTH: 58
<212> TYPE: DNA
<213> ORGANISM: Artificial
<220> FEATURE:
<223> OTHER INFORMATION: the first probe
<220> FEATURE:
<221> NAME/KEY: misc_feature
<222> LOCATION: (31)..(37)
<223> OTHER INFORMATION: n is a, c, g, or t
```

```
<220> FEATURE:
<221> NAME/KEY: misc_feature
<222> LOCATION: (58)..(58)
<223> OTHER INFORMATION: n is a, c, g, or t

<400> SEQUENCE: 1
ccatctcatc cctgcgtgtc tccgactcag nnnnnnntcg cgtattttt tttttvn            58

<210> SEQ ID NO 2
<211> LENGTH: 51
<212> TYPE: DNA
<213> ORGANISM: Artificial
<220> FEATURE:
<223> OTHER INFORMATION: the second probe
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (45)..(51)
<223> OTHER INFORMATION: n is a, c, g, or t

<400> SEQUENCE: 2
ccatctcatc cctgcgtgtc tccgactcag nnnnnnntcg cgtannnnnn n                 51

<210> SEQ ID NO 3
<211> LENGTH: 11
<212> TYPE: DNA
<213> ORGANISM: Artificial
<220> FEATURE:
<223> OTHER INFORMATION: forward primer

<400> SEQUENCE: 3
ccatctcatc c                                                             11

<210> SEQ ID NO 4
<211> LENGTH: 33
<212> TYPE: DNA
<213> ORGANISM: Artificial
<220> FEATURE:
<223> OTHER INFORMATION: reverse primer
<220> FEATURE:
<221> NAME/KEY: misc_feature
<222> LOCATION: (24)..(33)
<223> OTHER INFORMATION: n is a, c, g, or t

<400> SEQUENCE: 4
cctctctatg ggcagtcggt gatnnnnnnn nnn                                     33

<210> SEQ ID NO 5
<211> LENGTH: 58
<212> TYPE: DNA
<213> ORGANISM: Artificial
<220> FEATURE:
<223> OTHER INFORMATION: the first probe
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 5
ccatctcatc cctgcgtgtc tccgactcag nnnnnnntat cgcgttttt tttttvn            58
```

```
<210> SEQ ID NO 6
<211> LENGTH: 33
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (24)..(33)
<223> OTHER INFORMATION: n is a, c, g, or t

<400> SEQUENCE: 6
cctctctatg ggcagtcggt gatnnnnnnn nnn                               33

<210> SEQ ID NO 7
<211> LENGTH: 30
<212> TYPE: DNA
<213> ORGANISM: Artificial
<220> FEATURE:
<223> OTHER INFORMATION: reverse primer

<400> SEQUENCE: 7
tttttttttt tttttttttt tttttttttt                                  30

<210> SEQ ID NO 8
<211> LENGTH: 15
<212> TYPE: DNA
<213> ORGANISM: Artificial
<220> FEATURE:
<223> OTHER INFORMATION: forward primer

<400> SEQUENCE: 8
ccatctcatc cctgc                                                  15

<210> SEQ ID NO 9
<211> LENGTH: 64
<212> TYPE: DNA
<213> ORGANISM: Artificial
<220> FEATURE:
<223> OTHER INFORMATION: the first probe
<220> FEATURE:
<221> NAME/KEY: misc_feature
<222> LOCATION: (31)..(37)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t

<400> SEQUENCE: 9
ccatctcatc cctgcgtgtc tccgactcag nnnnnnntcg cgtattttt tttttttttt   60 ttvn                                                              64
```

GENE ANALYSIS SYSTEM

TECHNICAL FIELD

The present invention relates to a system for analyzing an arbitrary gene region, and in particular, to a system, a method, and a kit that are capable of analyzing information of an arbitrary gene region at a single cell level.

BACKGROUND ART

Organisms transcribe gene information held on a genome to mRNAs (gene expression) and synthesize proteins based on the information. The organisms then perform biological activities by the biological functions of the proteins. In recent years, studies have been increasingly proceeding for collectively understanding organisms by comprehensively analyzing such biological functions at a molecular level. Based on the findings obtained by the comprehensive analysis, for example, functions of pathologic cells and immune cells can be elucidated, which can be applied to elucidation of causes of diseases and development of new drugs.

As a means for comprehensive analysis, a genomic analysis which enables directly obtaining the information of a biological function and a gene expression analysis based on the expression level and the sequence of an mRNA are attracting attentions. As a sample for the analysis, in general, a tissue composed of a large number of cells and cultured cells are used. However, even in cells in the same tissue, the state of the gene expression is different from cell to cell or from time to time. Accordingly, for correctly understanding the function of a tissue in detail, it is necessary to analyze not plural cells but each cell in cells constituting the tissue to collectively understand the entire tissue based on the information of the gene expression. Among methods for analyzing the gene expression in a single cell, the technical development of the high throughput next generation DNA sequencer in recent years has made it possible to know the state of gene expression in detail for a huge number of genes.

In a biological tissue to be analyzed, cells do not act independently but correlate with one another while mutually exchanging information. Thus, in order to understand the detail of a biological phenomenon, a single-cell analysis including the positional information of the cell has to be made for many cells that are present around the cell to be analyzed. The number of the cells constituting the cell group to be analyzed is as many as several hundreds, or in some cases, several tens of thousands or more. When the gene expression analysis is performed for each cell in a cell group, there is a need to perform reactions in separate reaction vessels from one cell to another. As a general means for separating cells one-by-one and putting each cell into each individual reaction vessel, a cell sorter or a device having micro channels is used. However, in such a method, since cells have to be separated into individual cells in advance, the positional information of a cell can not be correlated to the analysis data of the gene expression. In addition, when reagents are dispensed into the reaction vessels, a manual or robot operation is assumed, and the quantities of the reaction solutions containing the reagents are in the order of microliters in terms of the precision of the dispensing. Thus, the more the number of the cells to be analyzed, the higher the cost of the reagents.

As an approach for solving the problem, PTLs 1-3 disclose methods for producing a complementary DNA (cDNA) library utilizing a porous membrane and a slide glass. In the methods, by placing a large number of cells or a biological tissue section on a device to extract mRNAs, the mRNAs can be captured on a cell-by-cell basis in plural areas each present just under each cell. For this reason, when a tag sequence having a different sequence for each area in which a cell is captured (hereinunder, referred to as cell holding area) and a nucleic acid probe having a sequence for capturing the extracted mRNA are disposed on the device to thereby synthesize a cDNA with each nucleic acid probe as a starting point, a different tag sequence for each cell can be introduced in the cDNA. Using the cDNA library array composed of plural cell holding areas constructed by this production method, gene sequences including the tag sequences are collectively analyzed by a high throughput DNA sequencer, whereby it is possible to analyze gene expression derived from single cell while maintaining the positional information. In addition, it becomes possible to process a large number of cells one-by-one in parallel on a device, and therefore the amount of the regents required can be reduced to about $1/100$ or less to reduce the regent cost. However, in this method, the tag sequence can be introduced only into a sequence on the 3' end of mRNA. In the analysis by a high throughput DNA sequencer, the length has to be adjusted to a length convenient in the base sequence analysis. However, when an arbitrary gene region is analyzed by a current method, a cDNA has to be digested to a convenient length before the tag sequence is introduced into digested fragments. In this case, when the cDNA is digested, the digested fragments are present in a mixed manner among the cell holding areas on the device. Furthermore, a method in which a complementary sequence having a convenient length is synthesized by a random sequence with a tag sequence using an mRNA or a cDNA as a template may be conceived. However, since a random sequence with a different tag sequence has to be introduced for each cell holding area on the device, it is necessary to use a robot, resulting in a problem of difficulty of the reagent cost reduction.

CITATION LIST

Patent Literature

PTL 1: WO 2011/068088
PTL 2: WO 2014/020657
PTL 3: US 2014/0066318

SUMMARY OF INVENTION

Technical Problem

For solving the above problems, an object of the present invention is to develop and provide a gene analysis system that enables identification of an arbitrary gene region of a gene derived from each of cells, by using a device including plural cell holding areas in which a cDNA library derived from single cell can be created in each of cell holding areas. Another object is to provide a method for collectively analyzing gene expression of a group of several hundred or more cells on a cell-by-cell basis while maintaining the positional information, using the gene analysis system.

Solution to Problem

As a result of intensive studies for solving the above problems, the present inventors have developed a new technique of producing a cDNA using as a template an mRNA derived from single cell or plural cells captured on and inside a device including plural cell holding areas, and then capturing the cDNA again without mixing the cDNAs among the areas, in which a tag sequence unique for each of the areas can be introduced into the cDNAs.

That is, the present invention includes the followings.

(1) A gene analysis system, including:
a single strand nucleic acid capturing means including a cell holding area arranged on a substrate, and a first probe that is placed in the cell holding area and has a sequence for capturing a single strand nucleic acid extracted from a cell;
a reaction product synthesizing means for synthesizing a nucleic acid having a sequence that is the same as or complementary to the captured single strand nucleic acid as a reaction product in the cell holding area;
a reaction product capturing means including a second probe that is placed in the cell holding area and has a sequence for capturing the reaction product;
a tag sequence introducing means for synthesizing a tag sequence-introduced product having a sequence that is the same as or complementary to a nucleic acid of the reaction product, and having a tag sequence unique for the cell holding area; and
a nucleic acid amplifying means for amplifying the tag sequence-introduced product.

(2) The system according to (1), wherein
the reaction product synthesizing means is for synthesizing a nucleic acid complementary to the captured single strand nucleic acid as a reaction product in the cell holding area, and
the tag sequence introducing means is for synthesizing a tag sequence-introduced product having a sequence complementary to a nucleic acid of the reaction product.

(3) The system according to (1), wherein
the reaction product synthesizing means is for synthesizing a nucleic acid having a sequence complementary to the captured single strand nucleic acid as a first reaction product in the cell holding area, and then synthesizing a nucleic acid having a sequence complementary to a nucleic acid of the first reaction product as a second reaction product, and
the tag sequence introducing means is for synthesizing a tag sequence-introduced product having a sequence complementary to a nucleic acid of the second reaction product.

(4) The system according to any one of (1) to (3), wherein the first probe and the second probe have different sequences, and the second probe has a tag sequence unique for each cell holding area.

(5) The system according to any one of (1) to (3), wherein the first probe and the second probe are the same probe, and have a tag sequence unique for each cell holding area.

(6) The system according to any one of (1) to (5), wherein the second probe further includes a common sequence that functions as a primer for amplifying a nucleic acid, and/or a nucleic acid amplification correcting sequence.

(7) The system according to any one of (1) to (6), wherein the reaction product is synthesized by using a primer including a sequence complementary to a part of the single strand nucleic acid.

(8) The system according to (7), wherein the primer further includes a common sequence that functions as a primer for amplifying a nucleic acid.

(9) The system according to any one of (1) to (8), wherein the first probe and/or the second probe is immobilized on the same carrier or on different carriers held in the cell holding area.

(10) The system according to any one of (1) to (9), wherein the first probe and/or the second probe is immobilized on the cell holding area or a carrier held in the cell holding area via a joint molecule.

(11) The system according to any one of (6) to (10), wherein the nucleic acid amplifying means is for performing amplification by an enzyme reaction using the common sequence and a sequence complementary to a sequence of the tag sequence-introduced product.

(12) A method for analyzing a gene, comprising:
a step of holding a cell in a sample in an area capable of holding a cell;
a step of capturing a single strand nucleic acid extracted from the cell by hybridization with a first probe;
a step of synthesizing a nucleic acid having a sequence that is the same as or complementary to the single strand nucleic acid as a reaction product;
a step of capturing the reaction product by hybridization with a second probe that is the same as or different from the first probe, has a sequence for capturing the reaction product, and has a tag sequence unique for the area;
a tag sequence introducing step of synthesizing a tag sequence-introduced product that has a sequence that is the same as or complementary to a nucleic acid of the reaction product, and has the tag sequence unique for the cell holding area, with the second probe coupled thereto; and
a step of amplifying the tag sequence-introduced product.

(13) A kit for analyzing a gene, for use in the method according to (12), including:
a gene analysis device, including a substrate that includes a single cell holding area or a plurality of cell holding areas, a first probe that is placed in the cell holding area and includes a sequence complementary to a single strand nucleic acid extracted from a cell, and a second probe that is placed in the cell holding area and has a sequence for capturing the reaction product;
an enzyme and a reaction reagent to be used in the steps; and nucleotides for synthesizing a nucleic acid.

(14) The kit for analyzing a gene, including:
a gene analysis device, including a substrate that includes a single cell holding area or a plurality of cell holding areas, a first probe that is placed in the cell holding area and includes a sequence complementary to a single strand nucleic acid extracted from a cell, and a second probe that is placed in the cell holding area and has a sequence for capturing the reaction product;
an enzyme and a reaction reagent to be used in the steps; and
nucleotides for synthesizing a nucleic acid, wherein the kit includes a primer that can hybridize with a part of the single strand nucleic acid to synthesize a reaction product.

(15) The kit according to (13) or (14), wherein the enzyme includes an enzyme for specifically adding a nucleic acid to an end of a reaction product.

Advantageous Effects of Invention

According to the present invention, it is possible to comprehensively analyze gene information of a large number of cells on a cell-by-cell basis with labor of the same level as for analysis of a single cell.

In addition, the present invention can be applied to genetic diagnosis, drug development, elucidation of diseases such as cancer, and regenerative medicine and can also contribute to progress of the life science.

BRIEF DESCRIPTION OF DRAWINGS

FIG. 1-2 shows schematic drawings of another embodiment of the substrate configuration in the gene analysis system of the present invention. (d) shows a mode in which each cell is held in one cell holding area and probes are immobilized to carriers, and (e) shows a mode in which each cell is held in one cell holding area and probes are directly immobilized to a porous membrane.

FIG. 2 is a diagram schematically showing an example of the nucleic acid probe configuration and the reaction steps in the gene analysis system used in Example 1.

DESCRIPTION OF EMBODIMENTS

1. Gene Analysis System

Figure 1:
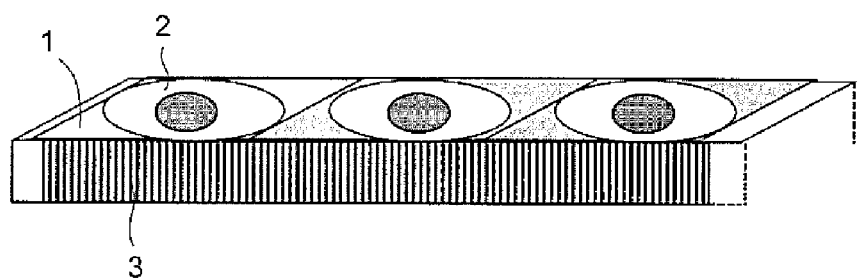
FIG. 1-1 shows schematic drawings of an embodiment of the substrate configuration of the gene analysis system of the present invention. (a) shows a mode in which each cell is held in one cell holding area and probes are directly immobilized to a porous membrane, (b) shows a mode in which one cell is held in plural cell holding areas and probes are directly immobilized to a porous membrane, and (c) shows a mode in which plural cells are held in one cell holding area and probes are directly immobilized to a porous membrane.
Figure 1:
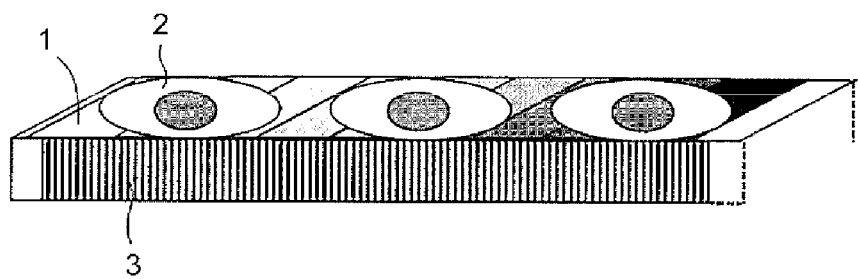
Figure 1:
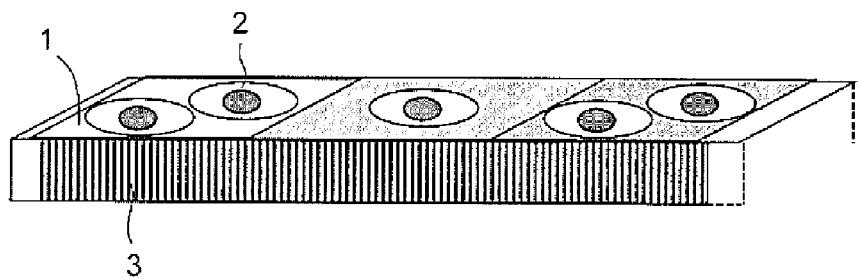
Figure 1:
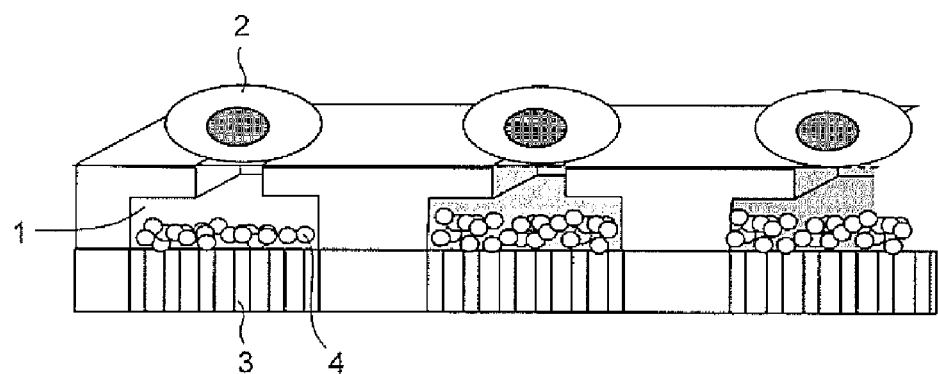

A configuration of the gene analysis system of the present invention will be described. The gene analysis system of the present invention includes a device including a substrate, and a first probe and/or a second probe as essential components.

1-1. Substrate

In the gene analysis system of the present invention, the "substrate" means a support including one cell holding area or plural cell holding areas.

The material of which the substrate is made is not particularly limited as long as it is a material generally used in the art for analyzing gene expression of DNAs and RNAs. Examples thereof include a metal, such as gold, silver, copper, aluminum, tungsten, molybdenum, chromium, platinum, titanium, and nickel, and an alloy, e.g., a stainless steel; silicon; a glass material, such as a glass, a quartz glass, a fused quartz, a synthetic quartz, an alumina, and a photosensitive glass (these materials are basically transparent); a plastic, such as a polyester resin, polystyrene, a polyethylene resin, a polypropylene resin, an ABS resin (acrylonitrile butadiene styrene resin), nylon, an acrylic resin, and a vinyl chloride resin (these materials are generally not transparent, but the materials is desirably made transparent so as to enable optical measurements); agarose, dextran, cellulose, polyvinyl alcohol, nitrocellulose, chitin, and chitosan.

The substrate may be made of two or more different materials. For example, as the case of a substrate having a sheet with pores (porous membrane) at the bottom thereof, the following case is exemplified: the frame of the substrate is made of a plastic or a metal as described above, and the sheet with pores is made of, for example, a film of an alumina, a glass, silicon, or the like; a gel thin film of an acrylamide gel, a gelatin, a modified polyethylene glycol, a modified polyvinyl pyrrolidone, and a hydrogel; or cellulose acetate, nitrocellulose, or a mixed membrane thereof, and a membrane of nylon membrane.

The substrate may be subjected to a processing such as housing as required. In addition, the substrate is preferably made of a material that is transparent to light having a wavelength in at least a part of the range of 300 nm to 10000 nm, that is, can transmit the light having such a wavelength. The reason is that the analysis of the gene expression can be performed optically on the substrate in this case.

The "cell holding area" means a partition of a minute space arranged on the substrate, and can be configured in a manner that plural cells supplied onto the substrate can be held on a cell-by-cell basis. The shape of the cell holding area is not particularly limited. For example, a planer-, a cylinder-, a substantial cylinder-, an elliptic cylinder-, a substantial elliptic cylinder-, a rectangular parallelpiped-, a substantial rectangular parallelpiped-, a cubic-, a substantially cubic-, a conic-, a substantially conic-, a pyramid-, and a substantial pyramid-shape can be applied. The opening diameter of the cell holding area may be any diameter as long as it is slightly smaller than the cell diameter or one cell can be just put in the area. That is, one cell may be held by plural areas or by one area. For example, the diameter may be in the range of 5 μm to 50 μm. Alternatively, plural cells may be held by one area. The depth of the cell holding area may be any depth as long as one cell is just put in the area, and, for example, the depth is in the range of 5 to 100 μm. In addition, in cases where a tissue section or the like is analyzed, the depth and the area are not limited to the above ranges. In other words, one area may hold all or part of plural cells. The number of the cell holding areas per substrate is not particularly limited. In general, the number may be in the range of 10 to $10^5$. The cell holding area is capable of functioning as a reaction cell on or inside the substrate.

The cell holding area has a first probe and/or a second probe described later placed therein, and may have a configuration in which a cell and the probe are present in the same partition and a nucleic acid extracted from the cell is captured by the probe present in the same partition, or a configuration in which a cell and the probe are present in different partitions and a nucleic acid extracted from the cell moves into another partition and is captured by the probe present therein.

1-2. First Probe

In the gene analysis system of the present invention, the "first probe" means a probe formed of a nucleic acid. The first probe is formed of a DNA in principle, but not limited thereto, and may include, for example, an RNA or an artificial nucleic acid.

The first probe includes a sequence for capturing a nucleic acid extracted from a cell (hereinafter, referred to as nucleic acid capturing sequence), and is placed in the cell holding area. As required, the first probe further includes a tag sequence and/or a common sequence and/or a nucleic acid amplification correcting sequence. The sequences constituting the first probe will be concretely described below.

The "nucleic acid capturing sequence" means an essential sequence constituting the first probe. The nucleic acid capturing sequence includes a sequence complementary to a part of a base sequence of a single strand nucleic acid extracted from a cell held in the cell holding area, or a random sequence, and configured to capture the extracted single strand nucleic acid. The base sequence of the nucleic acid capturing sequence is not particularly limited as long as it can hybridize with the target single strand nucleic acid to capture the single strand nucleic acid. Thus, the base sequence may be appropriately designed taking into account the kind and the sequence of the nucleic acid. In the present invention, examples of the target single strand nucleic acid include a messenger RNA (mRNA), a noncoding RNA (ncRNA), a micro-RNA, and a single strand DNA, and fragments thereof. The length of the nucleic acid capturing sequence may be any length that enables capturing the target single strand nucleic acid by hybridization. The nucleic acid capturing sequence is preferably a sequence complementary to a sequence on or near the 3' end side of the base sequence of the single strand nucleic acid.

For example, in the case where the target single strand nucleic acid is an mRNA, as the nucleic acid capturing sequence, an oligo (dT) sequence complementary to a poly-A sequence which is a part of the mRNA sequence can be used. The polymerization degree of dT which constitutes the oligo (dT) sequence may be any degree that enables capturing the poly-A sequence of the mRNA by hybridization. For example, the number of dTs may be 8 to 40, and preferably 8 to 30. In the case where an oligo (dT) sequence is used as the nucleic acid capturing sequence, it is preferred that a two-base random sequence is added to the 3' end thereof. By this addition, the efficiency of capturing the mRNA can be increased, and the amount of the artifact when a cDNA is synthesized can be significantly reduced. As such a random sequence, for example, a VN sequence (V is A, G, or C, and N is A, G, C, or T) is exemplified.

In addition, in the case where the target single strand nucleic acid is a single strand nucleic acid derived from a micro-RNA or a genome DNA, a random sequence can be used as the nucleic acid capturing sequence. Furthermore, by using a sequence complementary to a part of the base sequence of the single strand nucleic acid, only a target having a specific sequence can be captured.

The "tag sequence" means a selected sequence, which is an identification tag for each cell holding area and is to be put to a reaction product in the cell holding area. Accordingly, when there are plural cell holding areas, the tag sequence includes a base sequence unique for each cell holding area. The tag sequence is formed of a known base sequence having an arbitrary length. For example, when a tag sequence has a 5-base length, $4^5$ (=1024) kinds of different cell holding areas can each be given a unique tag sequence. In the same manner, for example, when a tag sequence has a 10-base length, $4^{10}$ (=1048576) kinds of different cell holding areas can each be given a unique tag sequence. Accordingly, the length of the tag sequence may be appropriately determined according to the positions and/or the number of the cell holding areas on the gene analysis system so that the cell holding areas can each be identified. Concretely, the length is preferably of 5 to 30 bases.

When there are plural cell holding areas on the substrate, the base sequence constituting the tag sequence varies from one cell holding area to another in principle, but a common base sequence may be shared by plural areas. For example, a case where each five cell holding areas on one substrate use a common tag sequence corresponds to the above. In this case, the five cell holding areas which share a common tag sequence may be considered as one cell holding area.

The "common sequence" means a selected sequence, which is a sequence capable of functioning as a forward (Fw) primer sequence for amplifying a reaction product in a nucleic acid amplifying step in a gene analysis method using the gene analysis system of the present invention. Accordingly, in principle, the common sequence is positioned on the 5' end side of a probe, but not limited thereto. The base length of the common sequence may be any length as long as it is a proper length as a primer. For example, the length is a 8 to 60-base length, and preferably a 10 to 50-base length. The base sequence of the common sequence is also not particularly limited, but preferably is designed to give a sequence having an appropriate Tm value as a primer sequence. The length is generally determined to give a Tm value of 50° C. or higher, and preferably 60° C. or higher.

The "nucleic acid amplification correcting sequence" means a sequence for correcting an amplification bias in a nucleic acid amplifying step in a gene analysis method using the gene analysis system of the present invention. In general, in the nucleic acid amplifying step, a bias occurs in the amplification efficiency of each nucleic acid fragment to be amplified according to various conditions, such as the length, the sequence configuration, and the position of the nucleic acid fragment, and therefore it is difficult to precisely quantify the amplified product. In the present method, when a different nucleic acid amplification correcting sequence is introduced to each nucleic acid fragment, in the sequence analysis, plural pieces of data having the same nucleic acid amplification correcting sequence can be considered as those derived from the same reaction product and corrected. For this reason, the amplification bias generated in each step can be corrected. The base length of the nucleic acid amplification correcting sequence is not particularly limited. For example, the length may be in the range of 5 to 30 bases, preferably 10 to 20 bases, and more preferably 10 to 15 bases. The base sequence of the nucleic acid amplification correcting sequence may also be designed to have a random sequence.

When the first probe includes, in addition to a nucleic acid capturing sequence, a tag sequence, a common sequence, and a nucleic acid amplification correcting sequence, the order of the sequences is not particularly limited, provided that the nucleic acid capturing sequence is positioned on the 3' end side of the first probe, and the common sequence is positioned on the 5' end side of the first probe.

The first probe, and the second probe described later (which are herein collectively called "nucleic acid probes") are placed in a cell holding area. By placing the nucleic acid probes in a cell holding area in advance, without damaging cells or a tissue, or without need of the later supply thereof to each cell area by a robot and the like, the gene information from a nucleic acid derived from each cell can be obtained. In particular, since the cell or tissue is not damaged, the change in gene expression caused by damage can be avoided.

As used herein, the "placing" means directly and/or indirectly immobilizing at a prescribed position by an appropriate method.

As an example of directly immobilizing a nucleic acid probe in a cell holding area, a case where the probe is immobilized on the inner surface of the cell holding area is exemplified. The position of immobilization is not limited. For example, probes may be immobilized on the bottom surface, the wall surface, or the entire surface of the cell holding area. Here, when the cell holding area has a porous membrane, the inner surface of the pores and the surface of the membrane fibers are included in the inner surface of the cell holding area.

As an example of indirectly immobilizing the first probe in the cell holding area, a case where the probe is immobilized on a surface of a carrier held on the inner surface of the cell holding area is exemplified. As used herein, the "carrier" means a mediator coupling a cell holding area and a nucleic acid probe. The carrier immobilizes the nucleic acid probe on the surface thereof, and the carrier itself is immobilized on the inner surface of the cell holding area so as to be separable as required. The material of the carrier is not limited, and for example, the carrier is made of a resin material (polystyrene, etc.), an oxide (glass, silica, etc.), a metal (iron, gold, platinum, silver, etc.), a polymer polysaccharide support (for example, Sepharose or Sephadex), a ceramic, a latex, and a combination thereof. The shape of the carrier is not particularly limited, but is preferably a spherical particle such as a bead, since such a shape has a large binding surface area and high operability. A magnetic bead is particularly suitable as a carrier in terms of the later collecting operation.

The nucleic acid probe may be placed in a cell holding area by any immobilization method known in the art. Examples of the immobilization method include biological binding, covalent binding, ionic binding, or physical adsorption to the inner surface of the cell holding area or to the surface of the carrier. In addition, it is possible to immobilize both the probes to the inner surface of the cell holding area and to the carrier via a spacer sequence.

Examples of the biological binding include binding via joint molecules, such as binding of biotin to avidin, streptavidin, or neutravidin, and binding of an antigen to an antibody. For example, the binding may be achieved by allowing an inner surface of a cell holding area or a carrier surface having avidin, streptavidin, or neutravidin bound thereto to react with a biotin-modified nucleic acid probe.

In cases of covalent binding, the binding can be achieved, for example, by introducing a functional group into a nucleic acid probe, introducing a functional group that is reactive with the former functional group onto an inner surface of a cell holding area or a carrier surface, and allowing the two functional groups to react with each other. Concretely, for example, covalent binding can be formed by introducing an amino group into a nucleic acid probe, and introducing an active ester group, an epoxy group, an aldehyde group, a carbodiimide group, an isothiocyanate group, or an isocyanate group onto an inner surface of a cell holding area or a carrier surface. Alternatively, it is possible to introduce a mercapto group into a nucleic acid probe and introduce an active ester group, a maleimide group, or a disulfide group onto an inner surface of a cell holding area or a carrier surface. As a method for introducing a functional group onto an inner surface of a cell holding area or a carrier surface, a method in which the inner surface of the cell holding area or the carrier surface is treated with a silane coupling agent having a desired functional group is exemplified. Examples of the silane coupling agent which can be used include γ-aminopropyltriethoxysilane, N-β-(aminoethyl)-γ-aminopropyltrimethoxysilane, and N-β-(aminoethyl)-β-aminopropylmethyldimethoxysilane. As another method for introducing a functional group onto an inner surface of a cell holding area or a carrier surface, a plasma treatment is exemplified.

As an example of the physical adsorption, a method in which an inner surface of a cell holding area or a carrier surface is subjected to a surface treatment with a polycation (polylysine, polyallylamine, polyethyleneimine, etc.) to effect electrostatic binding by use of the charge of the nucleic acid probe. Incidentally, the inside of the cell holding area or the carrier is preferably subjected to a surface coating in advance for preventing adsorption of other substances (a nucleic acid, a protein, etc.).

1-3. Second Probe

In the gene analysis system of the present invention, the "second probe" means a probe also formed of a nucleic acid as with the first probe. The second probe is also formed of a DNA in principle, but not limited thereto, and may include, for example, an RNA or an artificial nucleic acid.

Incidentally, in some embodiments of the present invention, the same nucleic acid probe can be used as the first probe and the second probe, but in this Description, for the descriptive purposes, a probe for capturing a single strand nucleic acid is referred to as a "first probe", and a probe for capturing a reaction product to amplify a tag sequence-introduced product is referred to as a "second probe".

The second probe includes as essential sequences a "sequence for capturing a reaction product derived from a single strand nucleic acid (hereinafter referred to as reaction product capturing sequence" and a "tag sequence", and is placed in a cell holding area. The second probe may further include, as required, a common sequence and/or a nucleic acid amplification correcting sequence. When the second probe includes a reaction product capturing sequence, a tag sequence, a common sequence, and/or a nucleic acid amplification correcting sequence, the order of the sequences is not particularly limited, provided that the reaction product capturing sequence is positioned on the 3' end side of the second probe and the common sequence is positioned on the 5' end side of the second probe.

The "reaction product", as used herein, means a reaction product derived from a single strand nucleic acid captured by the first probe. Concretely, the reaction product means a single strand nucleic acid having a complementary base sequence which is synthesized by an enzyme reaction using the former single strand nucleic acid or a complementary strand of the single strand nucleic acid as a template. Based on the above description, the "reaction product capturing sequence" includes a sequence complementary to a part of the base sequence of the reaction product, or a random sequence, and is configured to capture the synthesized reaction product. The base sequence of the reaction product capturing sequence is not particularly limited as long as it can hybridize with the target reaction product to capture the reaction product. For example, when the nucleic acid sequence is modified after producing the reaction product, a complementary sequence thereof is also included therein. Therefore, the reaction product capturing sequence can be appropriately designed taking into account the kind and the sequence of the nucleic acid which is the reaction product, the treatment after the reaction, and the like. In the present invention, examples of the target reaction product include a single strand DNA, but not limited thereto. The length of the reaction product capturing sequence may be any length that enables capturing the target reaction product by hybridization. The reaction product capturing sequence is preferably a sequence complementary to a sequence on or near the 3' end side of the base sequence of the reaction product.

The "tag sequence" is an essential sequence that constitutes the second probe and is an identification tag for each cell holding area and is to be put to a reaction product in a cell holding area. The tag sequence basically has the same configuration with the tag sequence described for the first probe, and as the tag sequences of the first and second probes present in the same cell holding area, the same sequence is preferably used.

The "common sequence" and the "nucleic acid amplification correcting sequence" have the same configurations as in the sequences described for the first probe, and thus the concrete explanation is omitted here.

2. Gene Analysis Method

The gene analysis method of the present invention will be described. The gene analysis method of the present invention uses the gene analysis system of the present invention.

The gene analysis method of the present invention includes the following first to sixth steps. The steps will be described below.

(First Step)

The "first step: cell holding step" is a step of causing plural cells to flow over the substrate in the gene analysis system of the present invention to allow each of the cell holding areas to hold one cell.

The sample used in the analysis in the present invention is not particularly limited as long as it is a sample derived from a living body to be analyzed for the gene expression, and any sample, such as a cell sample, a tissue sample, and a liquid sample, may be used. Concretely, a sample of a single cell, a sample containing plural cells, a tissue section sample, a sample arranged in an array form which hold plural individual cells in a two dimensional manner, and the like are exemplified.

The living body from which the sample is derived is not particularly limited, and a sample derived from any living body, such as a vertebrate (for example, a mammal, a bird, a reptile, a fish, an amphibian), an invertebrate (for example, an insect, a nematode, a crustacean), a protist, a plant, a fungus, a bacterium, and a virus may be used.

(Second Step)

The "second step: single strand nucleic acid capturing step" is a step of extracting a nucleic acid from the cell held in the cell holding area in the first step to capture the obtained single strand nucleic acid by a first probe in the cell holding area.

In the second step, the single strand nucleic acid extracted from the cell held in the cell holding area is captured by hybridization to the first probe placed in the cell holding area. In this step, the target single strand nucleic acid to be captured is not limited, but examples thereof include a messenger RNA (mRNA), a noncoding RNA (ncRNA), a micro-RNA, and a single strand DNA in a cell constituting a biological tissue, and a fragment thereof. The extraction of the nucleic acid from the cell may be conducted by any method known in the art. For example, the cell is lysed using a protease, such as Proteinase K, a chaotropic salt, such as guanidine thiocyanate and guanidine hydrochloride, a surfactant, such as Tween and SDS, or a commercially available reagent for cytolysis, whereby a nucleic acid included in the cell, that is, a DNA and an RNA can be eluted.

(Third Step)

The "third step: reaction product synthesizing step" is a step of synthesizing a reaction product derived from the single strand nucleic acid captured in the second step.

Figure 2:
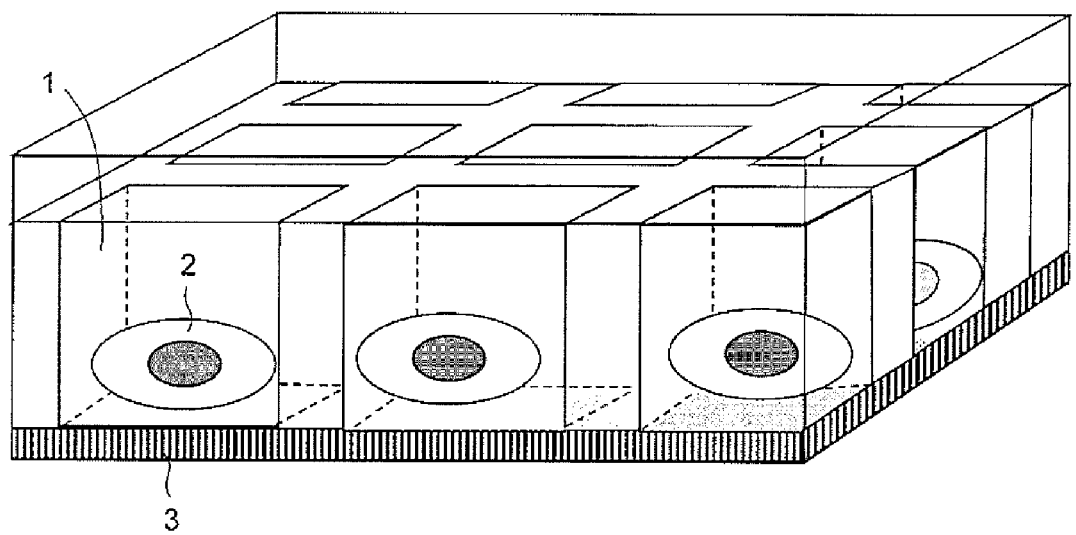
Figure 6:
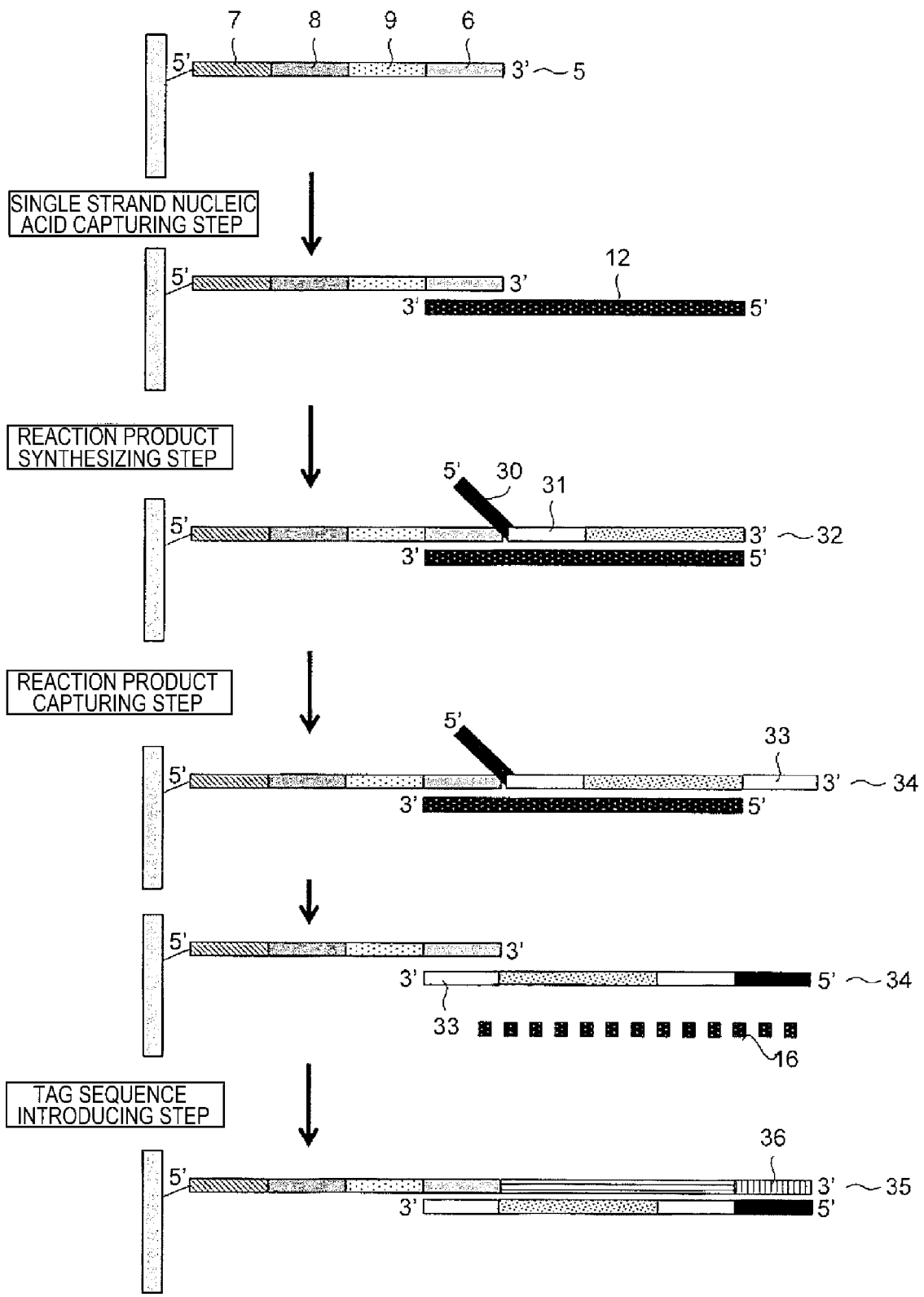
FIG. 6 is a diagram schematically showing an example of the nucleic acid probe configuration and the reaction steps in the gene analysis system of the present invention.
Figure 9:
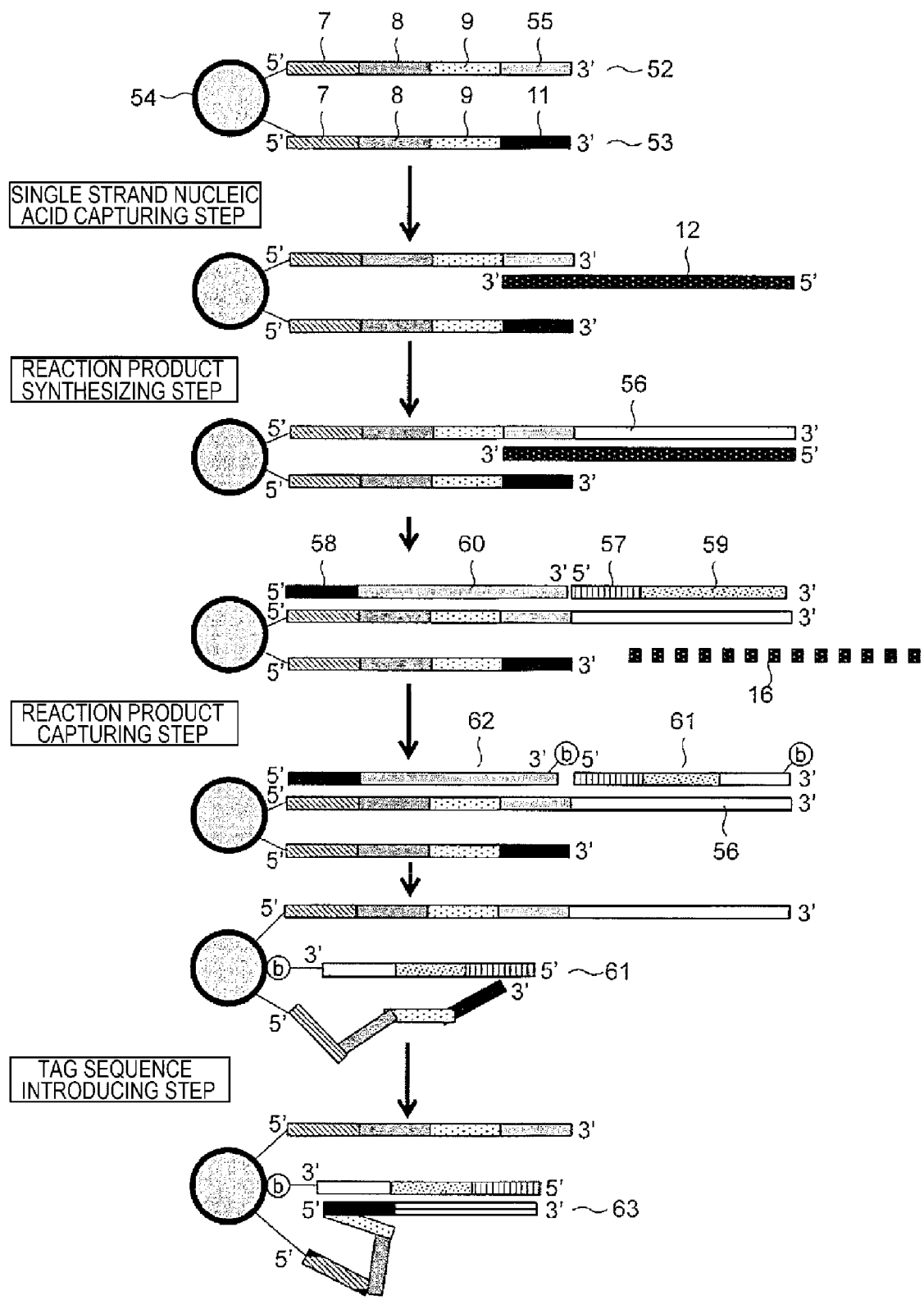
FIG. 9 is a diagram schematically showing an example of the nucleic acid probe configuration and the reaction steps in the gene analysis system of the present invention.

The reaction product in the third step can be synthesized with a reaction product synthesizing primer having a sequence complementary to a part of the captured single strand nucleic acid as a starting point (FIG. 2 and FIG. 6). Alternatively, the reaction product may be obtained in a manner that the captured single strand nucleic acid is used as a template to synthesize a complementary strand (a first reaction product) having the first probe coupled as a starting point, and then a reaction product synthesizing primer having a sequence complementary to a part of the complementary strand is used as a starting point to synthesize the reaction product (the second reaction product) (FIG. 9).

The reaction product synthesizing primer used here may be a random sequence, and is not particularly limited as long as it is a sequence that can hybridize with the nucleic acid used as the template (single strand nucleic acid or first reaction product) to synthesize the reaction product. In addition, a common sequence used in the sixth step (amplifying step) described later and/or a nucleic acid amplification correcting sequence may be added on the 5' end of the reaction product synthesizing primer (FIG. 6).

In the present invention, the synthesis of the reaction product (first and second reaction product in an embodiment shown in FIG. 9) may be conducted by any method known in the art. For example, when the single strand nucleic acid is an RNA such as mRNA, the reaction product can be synthesized, for example, by a reverse transcription reaction using a reverse transcriptase. In addition, when the nucleic acid is a DNA, the reaction product and the complementary strand may be synthesized by a replication reaction using a DNA polymerase. As an enzyme used for synthesizing the reaction product, an enzyme capable of performing strand displacement may be used. In this case, even when the reaction product synthesizing primers hybridize to positions close to each other, for example, within 100 bases, a reaction product having 100 bases or more can be obtained and therefore a reductant sequence analysis is possible, making it possible to enhance the accuracy of the sequence analysis.

(Fourth Step)

The "fourth step: reaction product capturing step" is a step of capturing the reaction product synthesized in the third step in the same cell holding area.

The reaction product derived from the single strand nucleic acid (or the second reaction product) is, after being separated from the corresponding single strand nucleic acid that has formed a double strand therewith (or the first reaction product), captured again in the same cell holding area in which the single strand nucleic acid has been captured. In some embodiments, the reaction product is directly bound to and captured on an inner surface of a cell holding area, a carrier surface, or the like in the vicinity of the second probe. The timing of the re-capture is desirably immediately after the separation of the reaction product from the template. As a method for the separation, an enzyme treatment with RNase H is mentioned when the template is an mRNA, and separation methods by a thermal denaturation and by a change of a buffer composition are mentioned in both the case of a DNA and the case of an RNA. By the re-capture in this step, the reaction product does not diffuse out into other cell capturing areas, making it possible to introduce a tag sequence derived from the same cell capturing area in a later step.

As a method for capturing the reaction product, a method of hybridization with a reaction product complementary sequence of the second probe placed in the same cell holding area may be mentioned. As another method for capturing the reaction product, a method of capturing the reaction product by modifying an end thereof may also be mentioned. For example, the reaction product can be captured by adding (a) nucleotide(s) (hereinafter referred to as nucleic acid modification sequence) to the 3' end of the reaction product. Concretely, for example, when a poly A is added to the 3' end of the reaction product using Terminal Deoxynucleotidyl Transferase (hereinafter referred to as TdT) and poly A polymerase, the reaction product having the poly A added can be captured by a second probe having a poly T sequence as the reaction product capturing sequence. Besides, by using a modification enzyme such as TdT, (a) nucleotide(s) other than adenine may also be added to the 3' end. In this case, the reaction product may be re-captured by using the second probe including a sequence complementary to the nucleic acid modification sequence.

In addition, as another method for capturing the reaction product, a method in which the reaction product is directly captured on the inner surface of the cell holding area in which the nucleic acid probe is held, or on a carrier held in the cell holding area may be mentioned. In this case, both the inner surface of the cell holding area or the carrier surface and the reaction product may be modified so as to enable the re-capture. As an example of such modification, a method may be exemplified in which avidin, streptavidin, or neutravidin is bound to the cell holding area surface or the carrier on which the nucleic acid probe is immobilized, and biotin is bound to the reaction product, whereby the reaction product is captured by the use of the specific binding of the two joint molecules (FIG. 9).

(Fifth Step)

The "fifth step: tag sequence introducing step" includes a step of introducing a tag sequence for each cell holding area into the captured reaction product.

After the reaction product is captured by the second probe in the fourth step, a complementary strand is synthesized in the fifth step by a DNA polymerase with the second probe as a starting point using the reaction product as a template. By this reaction, a sequence that is complementary to the reaction product is introduced with the second probe coupled thereto (referred to as tag sequence-introduced product). As a result, a tag sequence unique for the cell holding area can be introduced into a sequence derived from the reaction product (FIG. 2, FIG. 6).

When the reaction product is captured onto the inner surface of the cell holding area or on the carrier by binding of joint molecules in the fourth step, the reaction product is hybridized to the second probe that is held inside the cell holding area and exists in the vicinity of the capturing position, and a complementary strand coupled with the second probe as a starting point is synthesized by a DNA polymerase using the reaction product as a template, whereby a tag sequence can be introduced (FIG. 9).

(Sixth Step)

The "sixth step: amplifying step" represents a step of amplifying all or a part of the tag sequence-introduced product obtained in the fifth step.

In the amplifying step, a primer for amplification including a sequence complementary to the tag sequence-introduced product is hybridized to the product held on the inner surface of the cell holding area or the carrier to produce a complementary strand including sequences included in the second probe. As a primer for amplification for synthesizing the complementary strand, a reverse primer including a sequence complementary to the 3' end region of the tag sequence-introduced product may be used. In this case, the primer may have any sequence that is bound to the tag sequence-introduced product and serves as a starting point of the amplification reaction, and for example, a random sequence may also be used. In addition, it is possible that a common sequence (for example, a common reverse primer sequence having a sequence different from the common forward primer sequence included in the second probe) is added to the 5' end of the reaction product synthesizing primer, and the resulting sequence is used as a reverse primer (FIG. 6). Alternatively, the reverse primer may be designed to have a sequence specific to the target so as to amplify only a specific reaction product. Furthermore, it is also possible that (a) nucleotide(s) is further added to the 3' end of the tag sequence-introduced product, and a reverse primer including a complementary sequence to the nucleic acid-modified sequence is used.

After the complementary strand is synthesized, by performing an amplification reaction using the common sequence of the second probe (common forward primer) and the aforementioned reverse primer, it is possible to implement the amplifying step easily and efficiently. As the amplification method, any method known in the art can be used, and examples include the polymerase chain reaction (PCR), the nucleic acid sequence-based amplification (NASBA) method, the loop-mediated isothermal amplification (LAMP) method, and the rolling circle amplification (RCA) reaction. A person skilled in the art can appropriately design the second probe and the primer for amplification to be used according to the adopted amplification reaction.

Nucleic acid amplification is performed using the product obtained from the fifth step of the present invention as a template, and the amplified product can be analyzed for the gene sequence by any method known in the art. In addition, through the sequence analysis, the gene expression analysis is also possible. For example, in one embodiment, by determining the sequence of the amplified product, the presence or absence of the expression of the gene to be analyzed, the expression level (corrected based on the nucleic acid amplification correcting sequence), and the like can be analyzed. In the sequence analysis, according to a protocol of a large scale sequencer used in the analysis, an amplification primer sequence required may be designed into a common sequence for the forward primer and the reverse primer. In another embodiment, using a labeled probe having a sequence complementary to the tag sequence-introduced product, the probe is hybridized to a cDNA or the obtained amplified product, and the gene expression to be analyzed can be detected based on the label (for example, optically detected). The probe to be used for such detection can be appropriately designed by a person skilled in the art. Any label known in the art may be used as the label, and examples thereof include a fluorescent label (Cy3, fluorescein isothiocyanate (FITC), tetramethylrhodamine isothiocyanate (TRITC), etc.), a chemiluminescence label (luciferin, etc.), an enzymatic label (peroxidase, β-galactosidase, alkaline phosphatase, etc.), and a radioactive label (tritium, iodide$^{125}$, etc.). In another embodiment, by performing a nucleic acid amplification reaction using a probe having a sequence complementary to a sequence specific to the gene to detect the presence or absence of the amplification based on the chemiluminescence or fluorescence, the expression of the gene of interest can be analyzed.

In the present invention, by correlating the result of the gene analysis in the cDNA obtained in the above manner with a two dimensional positional information of the sample (cells, tissue, etc.), the correlation data between the particular position in the cells or tissue and the gene expression can also be obtained. Such two dimensional positional information of a sample is, for example, a micrograph of a cell sample or a tissue section sample, a fluorescence image or chemiluminescence image obtained by another labeling method, and the like.

3. Gene Analysis Kit

The present invention provides a kit for analyzing a gene from a single cell. The kit includes a device and a regent required in the use of the gene analysis system of the present invention, and the analysis can be achieved by the gene analysis method of the present invention. The kit is configured to include a substrate in which a first probe and/or a second probe is held in each cell holding area, and in addition, primers and enzymes, and other reagents required for an enzyme reaction. Examples of the enzymes include enzymes used for cytolysis and reaction product synthesis, for single strand nucleic acid decomposition, for reaction product modification, and for tag sequence introduction. The enzymes are described in the section 2, and the detail description is omitted here.

EXAMPLES

Concrete examples of embodiments of the present invention will be described below. However, the Examples are merely exemplified for realizing the present invention, and do not limit the present invention.

Example 1

This Example represents the following case. A substrate having plural cell holding areas (1) and a gene analysis system in which a first probe and a second probe are placed in each of the cell holding areas are used, and a single strand nucleic acid derived from a single cell captured by the first probe is used as a template to produce a reaction product, which is then captured by the second probe.

In the substrate in this configuration example, the plural cell holding areas (1) each of which can hold one cell or plural cells (2) are arranged in parallel. In FIGS. 1(a) to (c), the cell holding areas (1) each have a planer shape, and first probes and second probes are directly immobilized in a porous membrane (3) under each of the cell holding areas (1). In FIG. 1(d), the cell holding areas (1) are each composed of a cell holding portion having an opening diameter slightly smaller than the diameter of the cell (2) and a carrier holding portion in which carriers (4) having first probes and second probes immobilized thereon are held, and the cell holding areas (1) have the porous membrane (3) at the bottom surface thereof. In FIG. 1(e), the cell holding areas (1) are each composed of a cell holding portion having an opening diameter of approximately from 20 to 50 µm which is equal to or larger than the diameter of the cell (2) and the porous membrane (3) at the bottom surface thereof. As the configuration of the substrate in this Example, all the configurations described in FIG. 1 may be used.

In this Example, the single strand nucleic acid extracted from the cell is assumed to be an mRNA. Therefore, a first probe (5) shown in FIG. 2 has a base sequence represented by SEQ ID No. 1, for example, and includes on the 3' end side a nucleic acid capturing sequence (6) composed of an oligo (dT) sequence of 12 bases and a VN sequence of 2 bases. The first probe (5) is composed of, for example, a common sequence (7) of 30 bases, a nucleic acid amplification correcting sequence (8) formed of a random sequence of 7 bases, a tag sequence (9) of 7 bases, and the nucleic acid capturing sequence (6) of 14 bases in this order from the 5' end side. On the other hand, a second probe (10) has a base sequence represented by SEQ ID No. 2, for example, and is composed of the common sequence (7) of 30 bases, the nucleic acid amplification correcting sequence (8) formed of a random sequence of 7 bases, the tag sequence (9) of 7 bases, and a reaction product capturing sequence (11) formed of a random sequence of 7 bases in this order from the 5' end side.

As shown in FIG. 2, the reaction steps using the gene analysis system of this Example include: a cell holding step (I) in which an mRNA (12) which is a single strand nucleic acid is extracted from the cell (2) held in a cell holding area; a single strand nucleic acid capturing step (II) in which the mRNA (12) is captured by hybridization to the capturing sequence (6) in the first probe (5); a reaction product synthesizing step (III) in which using the captured mRNA (12) as a template, a reaction product synthesizing primer (13) formed of a random sequence of 7 bases having a sequence complementary to the mRNA is hybridized, and then a cDNA (reaction product) (14) is synthesized with the 3' end of the primer as a starting point; a reaction product capturing step (IV) in which the captured mRNA which is a single strand nucleic acid is degraded (16) and at the same time, a complementary sequence (15) of the reaction product capturing sequence in the reaction product (14) is immediately hybridized with the reaction product capturing sequence (11) in the second probe (10) to capture the reaction product; and a tag sequence introducing step (v) in which using the captured reaction product (14) as a template, a DNA strand (tag sequence-introduced product (17)) is synthesized from the 3' end of the second probe (10), thereby introducing the tag sequence into a sequence derived from the reaction product.

Figure 3:
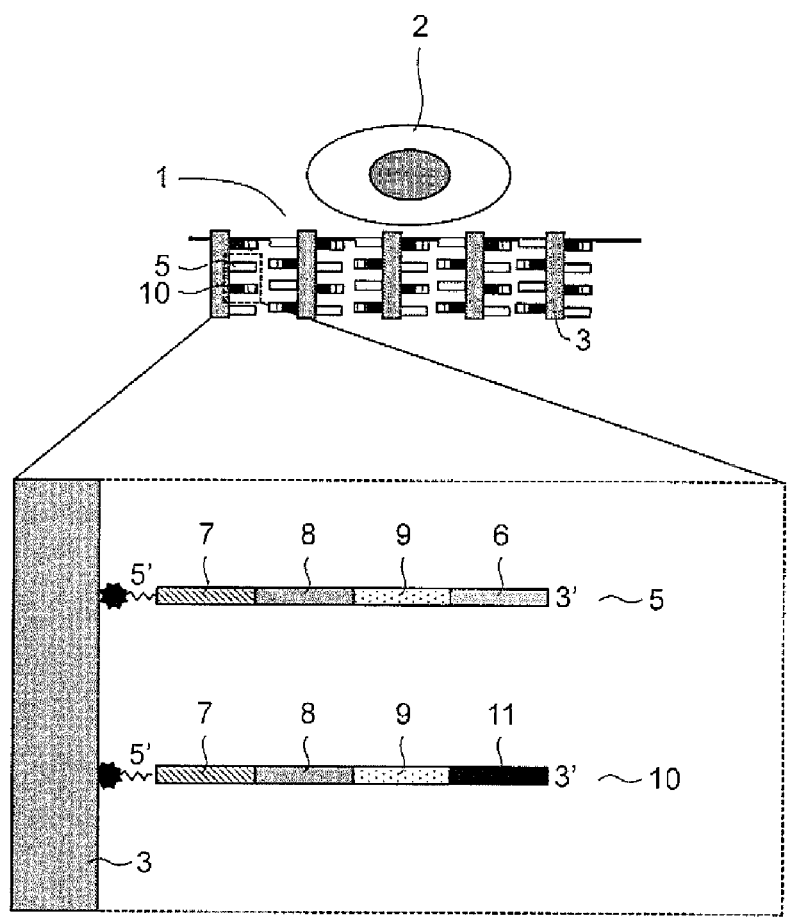
FIG. 3 is a diagram showing an example of the nucleic acid probe configuration in the gene analysis system of the present invention.

Next, an example of a configuration in which the first probes and the second probes are immobilized in the cell holding area (1) is shown in FIG. 3. FIG. 3 shows an example where the first probes (5) and the second probes (10) are immobilized on a porous surface of the porous membrane (3) forming the bottom of the cell holding area (1). The 5' end of each nucleic acid probe is modified with an amino group for immobilization, and directly immobilized on the porous membrane by covalent binding. In this Example, a commercially available Anodisc (GE Healthcare) having a pore size of approximately from 0.1 to 0.2 µm is used as the porous membrane. The thickness of the porous membrane is 60 µm, and nucleic acid probes can be immobilized on the surface. In general, a density of the nucleic acid probes that can be immobilized on the solid surface is 1 nucleic acid probe/30-100 nm$^2$, and therefore, about $5 \times 10^5$ nucleic acid probes can be immobilized in the inner wall of one pore. The volume of the pore is about $1.8 \times 10^{-16}$ L, and therefore, the density of the nucleic acid probes is 5 mM. For example, when the ratio of the nucleic acid probes immobilized on the porous membrane, first probes:second probes, is 1:5 or so, the density of the first probes is approximately 0.8 mM, and the density of the second probes is approximately 4 mM, which are both a sufficient concentration to perform the reaction in a high efficiency. The probability of the loss of the reaction product capture is also estimated to be 0% or less (Biophysical Journal, 69. 2243-2255 (1995), Biophysical Journal, 20. 193-219 (1997), Biophysical Journal, 66. 255-600 (1994)). However, this ratio can be varied depending on the conditions of the experiment, and is not limited thereto.

In this Example, a silane coupling agent for immobilizing the nucleic acid probes (5, 10) to the porous membrane (3) and a silanized MPC polymer for making the surface hydrophilic were simultaneously immobilized in an appropriate ratio to the porous surface by covalent binding, thereby achieving a high density immobilization of DNA. In practice, an Anodisc with a 0.1 μm pore size (GE Healthcare) was first immersed in an ethanol solution for 3 minutes, and then washed twice with a 0.1% Tween 20+10 mM Tris (pH 8.0) solution and dried. After that, the Anodisc was subjected to a $UVO_3$ treatment for 3 minutes, and immersed in an ethanol solution containing 3 mg/mL of a MPC monomer (for example, Langmuir 26. 13028-13032 (2010)) and 0.3 mg/mL of a silane coupling agent GTMSi (GTMSi: 3-glycidoxypropyltrimethoxy silane; Shinetsu Chemical) for 1 hour. After washing with ethanol, the Anodisc was treated with heat at 120° C. for 1 hour in an oven. Next, a PDMS sheet having partitions of a 20 μm diameter and having a thickness of 0.1 μm was superposed on the treated Anodisc. For immobilizing the nucleic acid probes (5, 10) to the porous membrane (3) in each partition on the PDMS sheet, 100 pL of a 0.05 M borate buffer (pH 8.5) containing the first probes (5) (1 mM), the second probes (10) (5 mM), 1% glycerol, and 0.15 M NaCl was ejected into each area on the sheet in a technique the same as in an inkjet printer. After that, in a humidification chamber, an epoxy group on the Anodisc and the amino group on the 5' end of the nucleic acid probe were allowed to react at 25° C. for 2 hours. Finally, unreacted functional groups on the Anodisc was blocked, and for removing the excess nucleic acid probes, the Anodisc was washed with a sufficient amount of a borate buffer (pH 8.5) containing 10 mM Lys, 0.01% SDS, and 0.15 M NaCl for 5 minutes. After removing the washing liquid, a 30 mM sodium citrate buffer (2×SSC, pH 7.0) containing 0.01% SDS and 0.3 M NaCl was used to wash the Anodisc at 60° C. to remove the excess DNA. In this manner, the immobilization and surface treatment of the nucleic acid probes were completed.

Next, a method for capturing cells using the gene analysis system having the above configuration will be described. First, about 1000 cells were washed with 500 μL of 1×PBS, and then 50 μL of 1×PBS cooled to 4° C. was added thereto to prepare a cell solution. The cell solution was arranged in an array form in the cell holding areas of FIG. 1(a). Concretely, a PDMS sheet having arranged thereon 1000 cell holding areas each having a partition of 20 μm sides with a thickness of 0.1 μm was laminated with an Anodisc for immobilizing probes to form a substrate of the gene analysis system of this Example. The cell solution was allowed to flow from the top toward the bottom of the substrate, and thus the cells were held in the respective cell holding areas, and the remaining solution was discharged from the bottom of the Anodisc as a waste fluid. In this manner, about 80% of the cells can be captured one-by-one in the respective cell holding areas.

Subsequently, the cells captured on the substrate were lysed by an ordinary method using a reagent for cytolysis, the obtained mRNA was captured by the first probe, and then by the aforementioned reaction steps, a tag sequence-introduced product was obtained. Incidentally, in this Example, SuperScript III (Invitrogen) was used in the reaction product synthesizing step (III) as a reverse transcriptase for synthesizing a complementary strand of an mRNA, RNase H (Invitrogen) was used in the reaction product capturing step (IV) as an enzyme for degrading the RNA, and Platinum Taq DNA polymerase High Fidelity (Life Technologies) was used in the tag sequence introducing step (V) as a DNA polymerase. The compositions of the cytolysis reagent, the reverse transcription reaction reagent, the RNase H reagent, and the DNA polymerase reaction reagent are shown in Tables 1 to 4.

TABLE 1

Composition of cytolysis reagent (all from Roche)

| Reagent | Concentration (final concentration) |
|---|---|
| Ready-to-use lysis buffer | ×1 |
| Protector RNase inhibitor | 1 U |

TABLE 2

Composition of reverse transcription reaction reagent (all from Invitrogen)

| Reagent | Concentration (final concentration) |
|---|---|
| ×5 RT Buffer | ×1 |
| 0.1M DTT | 0.02M |
| 40 U RNase OUT | 40 U |
| 10 mM dNTP mix | 1.5 mM |

TABLE 3

Composition of RNase H reaction reagent (all from Invitrogen)

| Reagent | Concentration (final concentration) |
|---|---|
| ×10 RT Buffer | ×1 |
| 50 mM $MgSO_4$ | 8.3 mM |
| 0.1M DTT | 0.2 mM |

TABLE 4

DNA polymerase reaction reagent (all from Life Technologies)

| Reagent | Concentration (final concentration) |
|---|---|
| ×10 RT High Fidelity buffer | ×1 |
| 50 mM $MgSO_4$ | 50 nM |
| 10 mM dNTP mix | 5 nM |

Figure 4:
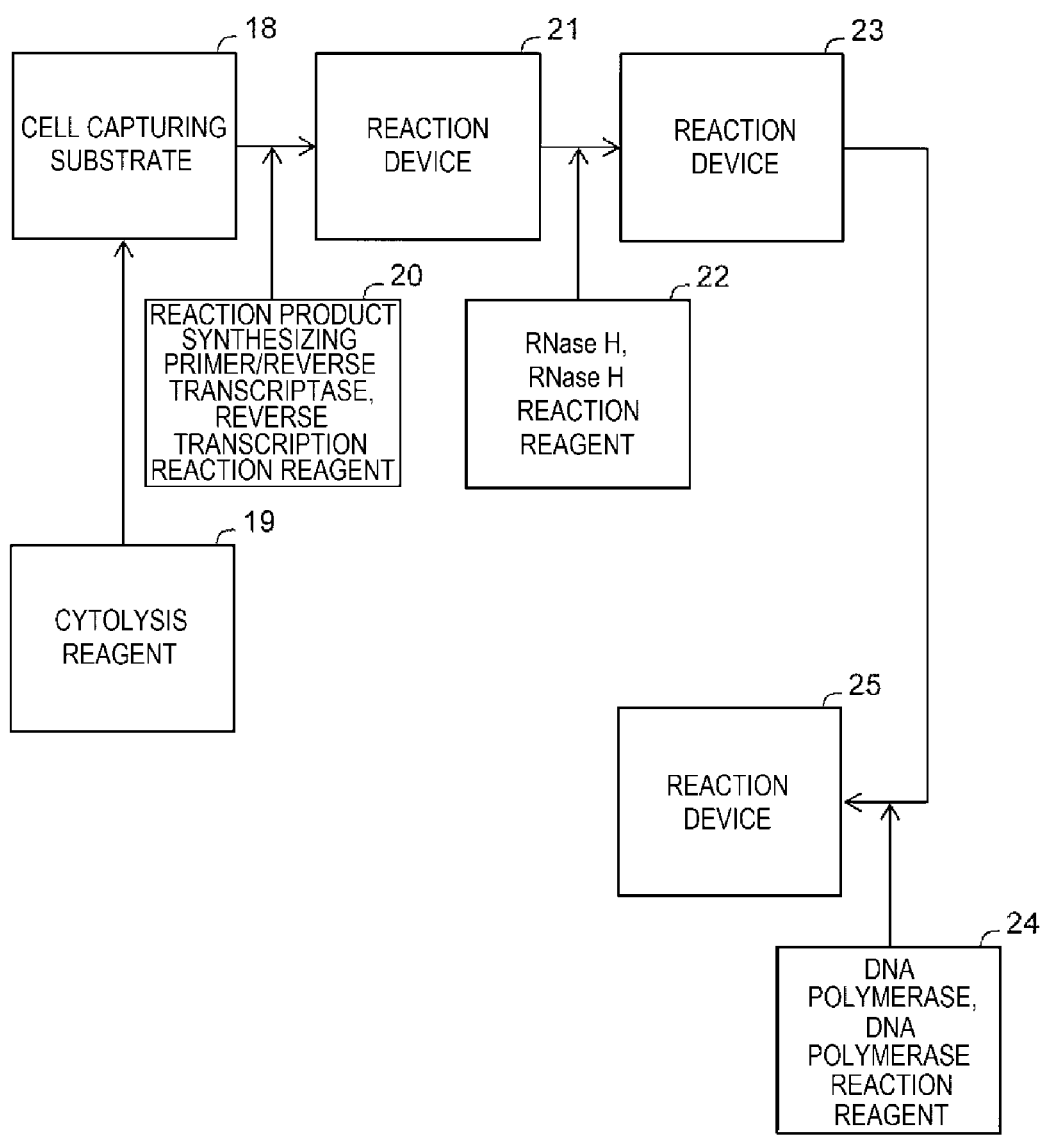
FIG. 4 is a diagram showing one embodiment of the reaction flow in the present invention.

Next, the reaction flow of this Example is shown in FIG. 4, and the concrete reaction conditions will be described below. Into a cell capturing substrate (18) formed of the aforementioned substrate in which about 1000 cells were captured, 5 μL of a cytolysis reagent (19) was added and allowed to stand at room temperature for 5 minutes to lyse the cells. At the same time with lysing the cells, an mRNA is captured by a first probe in a pore present in each cell holding area. Then, a reaction product synthesizing primer formed of a random sequence of 7 bases (1 μM) and 50 μL of a reaction liquid (20) composed of the reverse transcriptase (200 U) and the reverse transcription reaction reagent were added, and allowed to react in a reaction device (21) at room temperature for 10 minutes, at 37° C. for 10 minutes, and 48° C. for 50 minutes. Then, 5 μL of a reaction liquid (22) composed of the RNase H (60 U) and the RNase H reaction reagent was added and allowed to react in a reaction device (23) at 37° C. for 1 hour. Further, 10 μL of a reaction liquid (24) containing the DNA polymerase (5 U) and the DNA polymerase reaction reagent was added and allowed to react in a reaction device (25) at 98° C. for 10 seconds, at 40° C. for 1 minute, and at 68° C. for 1 minute, followed by lowering the temperature to 4° C. Through the above reactions, a cDNA (reaction product) having a complementary sequence to the base sequence of the captured mRNA was synthesized using the first probe as a primer, and the obtained reaction product was captured by the second probe during the treatment with the RNase H, and a DNA complementary strand was synthesized by the DNA polymerase, whereby a double strand reaction product having a tag sequence unique for each of the cell holding areas added could be obtained.

At the end, using as a template the tag sequence-introduced product (17) synthesized with the second probe coupled thereto obtained in this embodiment, the amplifying step (VI) was performed from the 5' end of the common sequence (7) using a forward primer of 11 bases (for example, represented by SEQ ID No. 3) and a reverse primer including a random sequence of 10 bases (for example, represented by SEQ ID No. 4), and the obtained amplified product was subjected to a sequence analysis. By acquiring information of the tag sequence contained in the amplified product, it is possible to determine a specific gene sequence for each area or each group of areas on a device.

In this Example, all or any of the single strand nucleic acid capturing step, the reaction product capturing step, and the tag sequence introducing step may be conducted at the same time.

Example 2

This Example represents the following case. The substrate shown in FIG. 1(b) having plural cell holding areas and a gene analysis system in which first probes shown in FIGS. 5 and 6 are placed in each of the plural cell holding areas are used, and a single strand nucleic acid derived from a single cell captured by the first probe is used as a template to produce a reaction product, which is then modified and captured again by the first probe.

The substrate in this configuration is configured so that plural cell holding areas hold one cell. The cell holding areas (1) are each composed of a cell holding portion having an opening diameter of approximately from 5 to 15 μm which is smaller than the diameter of the cell (2) and a porous membrane (3) of the bottom surface thereof (FIG. 1(b)).

Figure 5:
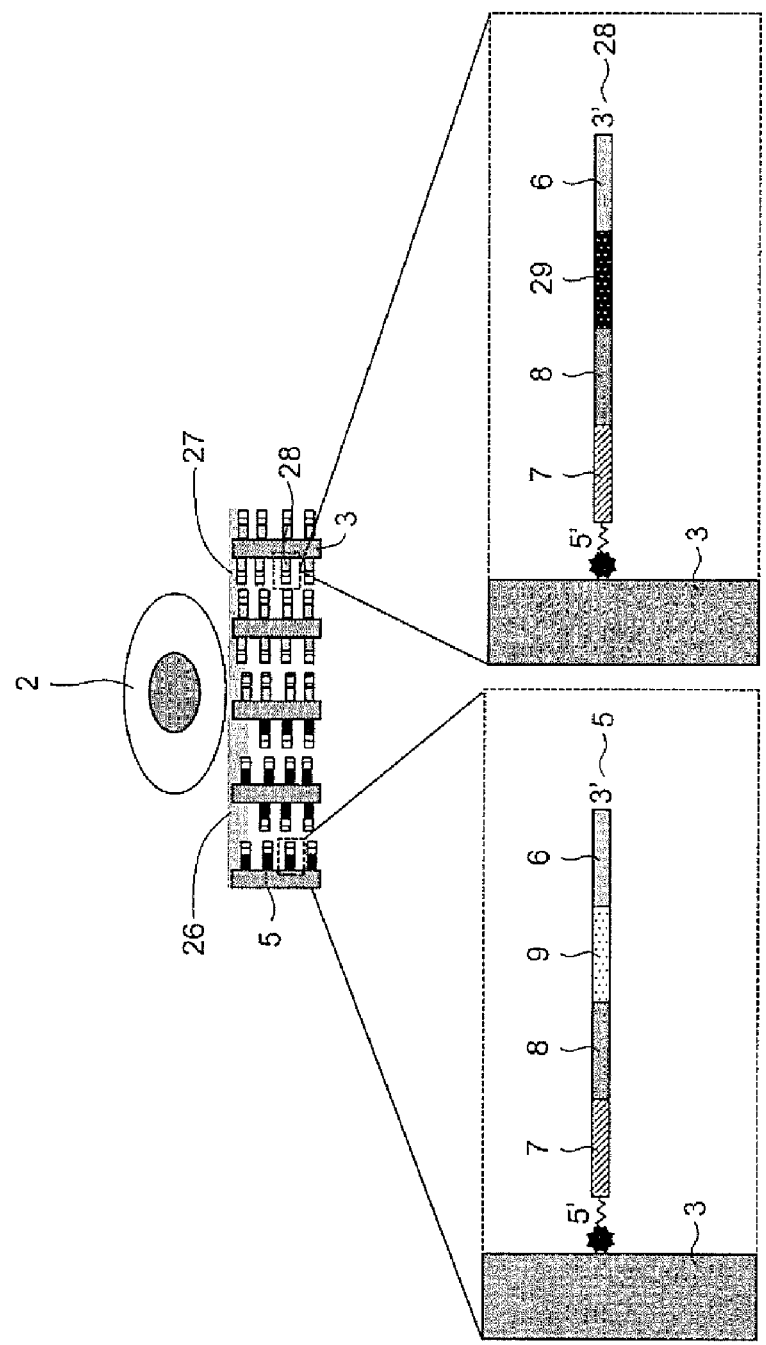
FIG. 5 is a diagram showing a nucleic acid probe configuration and an immobilization mode of a nucleic acid probe in the gene analysis system used in Example 2.

The first probe to be used in this Example is immobilized on a surface of a pore wall of the porous membrane (3) forming the bottom of cell holding areas (26) and (27) as shown in FIG. 5. Here, one cell is held on plural areas (two areas in FIG. 5), and the tag sequence (9) of the first probe (5) immobilized under the cell holding area (26) (for example, represented by SEQ ID No. 1) and the tag sequence (29) of the first probe (28) immobilized under the cell holding area (27) (for example, represented by SEQ ID No. 5) were different sequences.

In this Example, like in Example 1, the single strand nucleic acid extracted from the cell is assumed to be an mRNA. The first probes (5) and (28) were each composed of the common sequence (7) of 30 bases, the nucleic acid amplification correcting sequence (8) formed of a random sequence of 7 bases, the tag sequence (9) or (29) of 7 bases which is different for each area, and the nucleic acid capturing sequence (6) composed of an oligo (dT) sequence of 12 bases and a VN sequence of 2 bases, in this order from the 5' end thereof.

Next, reaction steps using the gene analysis system of this Example are shown in FIG. 6. Here, the case where only the first probe (5) is used as probes (that is, the first probe functions also as a second probe) will be described. The reaction steps include: a cell holding step (I) in which the mRNA (12) which is a single strand nucleic acid was extracted from the cell (2) held in a cell holding area; a single strand nucleic acid capturing step (II) in which the mRNA (12) is captured by hybridization to the capturing sequence (6) in the first probe (5); a reaction product synthesizing step (III) in which using the captured mRNA (12) as a template, a reaction product synthesizing primer (31) formed of a random sequence of 7 bases having a sequence complementary to the mRNA and having a common sequence (30) coupled at the 5' end (for example, represented by SEQ ID No. 6) is hybridized, and then a cDNA (reaction product) (32) is synthesized with the 3' end of the primer as a starting point; a reaction product capturing step (IV) in which a poly-A sequence (33) is added to the 3' end of the reaction product to produce a modified reaction product (34), and then the mRNA which is the captured single strand nucleic acid was degraded (16), and the poly-A sequence (33) of the modified reaction product (34) is immediately hybridized with the capturing sequence (6) of the first probe (5) to re-capture the modified reaction product (34); and a tag sequence introducing step (V) in which using the captured modified reaction product (34) as a template, a DNA strand (tag sequence-introduced product (35)) is synthesized from the 3' end of the first probe (5), thereby introducing the tag sequence and a complementary sequence (36) of the common sequence (30) into a sequence derived from the reaction product (cDNA).

In this Example, the nucleic acid modification to the 3' end of the reaction product may be made with a sequence other than a poly-A sequence. For example, a poly-T sequence may be added using TdT. In this case, by immobilizing as the capturing sequence (6) a second probe that is different from the first probe and includes a poly-A sequence into the cell holding area, the reaction product can be captured. Although the configuration of FIG. 1(b) is used in the reaction steps of this Example, all configurations shown in FIG. 1 may be used.

Next, a method for immobilizing the first probes (5) and (28) into the cell holding areas (26) and (27) will be described. The 5' end of each nucleic acid probe is modified with biotin for immobilization. In this Example, a commercially available Anodisc (GE Healthcare) having a pore size of approximately from 0.1 to 0.2 μm was used as the porous membrane. The immobilization density and the immobilization level are as described in Example 1.

In this Example, like in Example 1, a silane coupling agent and a silanized MPC polymer for maintaining hydrophilicity are simultaneously immobilized in an appropriate ratio by covalent binding to a pore surface, thereby achieving high density immobilization of DNA. In practice, first, an Anodisc with a 0.2 μm pore size (GE Healthcare) was immersed in an ethanol solution for 3 minutes, and then washed twice with a 0.1% Tween 20+10 mM Tris (pH 8.0) solution and dried. After that, a $UVO_3$ treatment was performed for 4 minutes, and the Anodisk was immersed in an ethanol solution containing 3 mg/mL of a MPC monomer (for example, Langmuir 26. 13028-13032 (2010)) and 0.3 mg/mL of a silane coupling agent GTMSi (GTMSi: 3-glycidoxypropyltrimethoxy silane; Shinestu Chemical) for 1 hour. After washing with ethanol, the Anodisc is subjected to a heat treatment at 120° C. for 1 hour in an oven. Next, the Anodisc was immersed in a streptavidin solution adjusted to 1 mg/mL for 16 hours under an environment of 4° C., allowing an epoxy group on the Anodisc to react with an amino group in streptavidin to achieve immobilization. A PDMS sheet having a thickness of 0.1 μm and having partitions of 5 μm sides was superposed on the thus treated Anodisc. For immobilizing the first probes (5, 28) on the porous membrane (3) in each partition on the PDMS sheet, 100 pL of a probe immobilization reagent containing the first probes (5 mM) (Table 5) was ejected into each area on the sheet by the same technique as in an inkjet printer. After that, streptavidin on the Anodisc was allowed to react with biotin on the 5' end of the nucleic acid probe at 37° C. for 1 hours. Finally, for removing the excess nucleic acid probes on the Anodisc, the Anodisc was washed with a borate buffer (pH 8.5) containing 0.01% SDS and 0.15 M NaCl for 5 minutes. After removing the washing liquid, a 30 mM sodium citrate buffer (2×SSC, pH 7.0) containing 0.01% SDS and 0.3 M NaCl was used to wash twice the Anodisc at 60° C. to remove the excess DNA. In this manner, the immobilization and the surface treatment of the nucleic acid probe were completed. After that, a PDMS sheet having a thickness of 0.1 μm and having partitions of 20 μm diameter was further superposed thereon. The method for capturing cells with the gene analysis system having the above configuration was the same method as in Example 1.

Subsequently, cells captured on the substrate were lysed using a cytolysis reagent according to an ordinary method, an obtained mRNA was captured by the first probe, and then a tag sequence-introduced product was obtained through the aforementioned reaction steps. In this Example, SuperScript III (Invitrogen) was used as a reverse transcriptase for synthesizing the complementary strand of the mRNA in the reaction product synthesizing step (III), TdT (Invitrogen) was used as a modification enzyme for modifying the end of the reaction product with poly-A and RNase H (Invitrogen) was used as an enzyme for degrading the RNA in the reaction product capturing step (IV), and Platinum Pfx DNA polymerase (Invitrogen) was used as a DNA polymerase used in the tag sequence introducing step (V). The compositions of the cytolysis reagent, the reverse transcription reaction reagent, and the RNase H reagent are the same as those shown in Tables 1 to 3. The composition of the modification enzyme reaction reagent in this Example is shown in Table 6, and the composition of the DNA polymerase reaction reagent is shown in Table 7.

TABLE 5

Probe immobilization reagent

| Reagent | Concentration (final concentration) |
|---|---|
| Tris-HCl (pH 8.0) | 20 mM |
| Tween 20 | 0.1% |
| EDTA | 1 mM |
| NaCl | 2M |

TABLE 6

Modification enzyme reaction reagent

| Reagent | Concentration (final concentration) |
|---|---|
| 10 mM dATP (Invitrogen) | 1.5 mM |
| GeneAmp 10× buffer (Life Technologies) | 1× |
| 5 mM MgCl$_2$ | 0.75 mM |

TABLE 7

DNA polymerase reaction reagent (all from Invitrogen)

| Reagent | Concentration (final concentration) |
|---|---|
| 10 mM dNTP | 0.3 mM each |
| 10 × Pfx Amplification buffer | 1× |
| 50 mM MgCl$_2$ | 1.0 mM |

Figure 7:
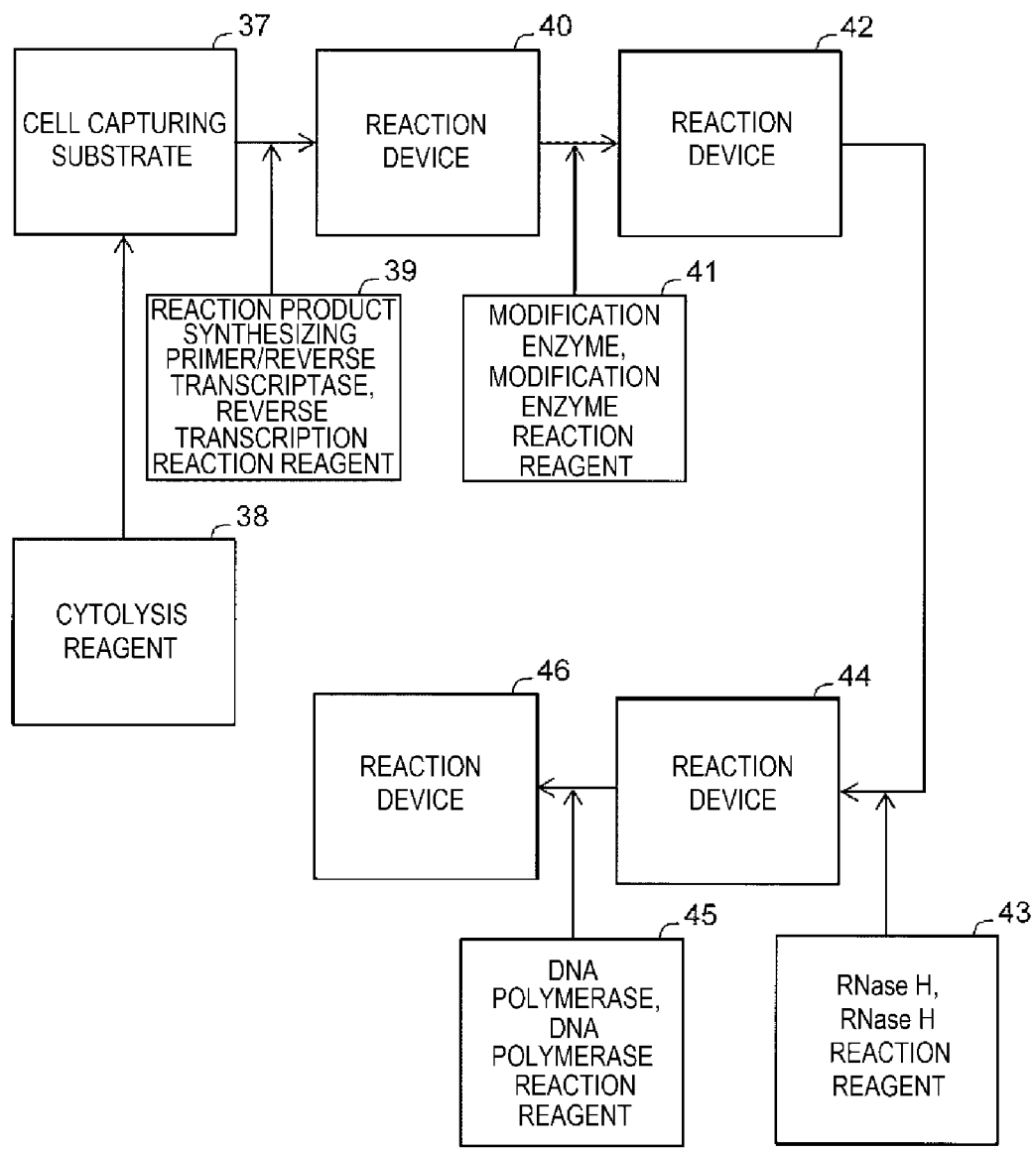
FIG. 7 is a diagram showing one embodiment of the reaction flow in the present invention.

The reaction flow of this Example is shown in FIG. 7 and the concrete reaction conditions will be described below. 5 μL of a cytolysis reagent (38) was added to a cell capturing substrate (37) formed of the aforementioned substrate in which about 1000 cells were captured, and allowed to stand at room temperature for 5 minutes to lyse the cells. At the same time with lysing the cells, an mRNA is captured by the first probe in a pore present in each cell holding area. Then, a reaction product synthesizing primer (1 μM) and a reaction liquid (39) composed of the reverse transcriptase (200 U) and the reverse transcription reaction reagent were sequentially added and allowed to react in a reaction device (40) at room temperature for 10 minutes, at 37° C. for 10 minutes, and at 48° C. for 50 minutes. Then, 20 μL of a reaction liquid (41) composed of the modification enzyme (0.2 U) and the modification enzyme reaction reagent was added and allowed to react in a reaction device (42) at 37° C. for 15 minutes. Next, 5 μL of a reaction liquid (43) composed of the RNase H (60 U) and the RNase H reaction reagent was added and allowed to react in a reaction device (44) at 37° C. for 30 minutes. Further, 10 μL of a reaction liquid (45) containing the DNA polymerase (1 U) and the DNA polymerase reaction reagent was added and allowed to react in a reaction device (46) at 94° C. for 15 seconds, at 40° C. for 30 seconds, and at 68° C. for 2 minutes, followed by lowering the temperature to 4° C. Through the above reactions, a cDNA having a sequence complementary to the base sequence of the mRNA captured by the first probe (reaction product) was synthesized. By modifying the 3' end of the reaction product with poly-A, then capturing the reaction product again by the first probe, and synthesizing a DNA chain by the DNA polymerase, a reaction product having a tag sequence unique for each cell holding area added could be obtained. At the end, using as a template the tag sequence-introduced product (35) synthesized with the first probe coupled thereto obtained by this embodiment, and using the common sequence (7) as a forward primer and the complementary sequence (36) of the common sequence (30) as a reverse primer, the amplifying step (VI) was performed, and the obtained product was subjected to a sequence analysis. By acquiring information of the tag sequence contained in the amplified product, it is possible to determine a specific gene sequence for each area or each group of areas on the device. In this Example, all or any of the reaction product modification reaction, the mRNA degradation, the reaction product capturing step, and the tag sequence introducing step may be conducted at the same time.

Example 3

This Example represents the following case. The substrate shown in FIG. 1(d) having plural separated cell holding areas and a gene analysis system shown in FIG. 8 in which first probes and second probes are placed in each of the cell holding areas are used, and a single strand nucleic acid derived from a single cell captured by the first probe is used as a template to produce a reaction product, which is then captured by the second probe.

The substrate in this configuration is configured so that each cell holding area holds one cell. The opening diameter of the cell holding area (1) is approximately from 5 to 15 µm which is smaller than the diameter of the cell (2). The substrate is composed of a through hole having the above opening diameter, a carrier holding portion in which carriers having the first probes and the second probes immobilized are held, and the porous membrane (3) of the bottom surface.

Figure 8:
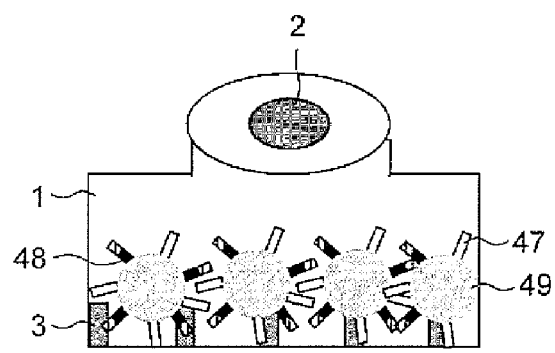
FIG. 8 is a diagram showing a substrate configuration, a nucleic acid probe configuration, and an immobilization mode of a nucleic acid probe in the gene analysis system used in Example 3. (a) and (b) each shows a configuration of a cell holding area in the substrate of the gene analysis system, and (c) shows an immobilization mode of nucleic acid probes onto a carrier.
Figure 8:
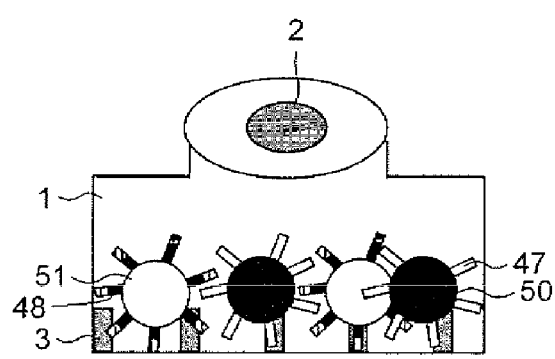
Figure 8:
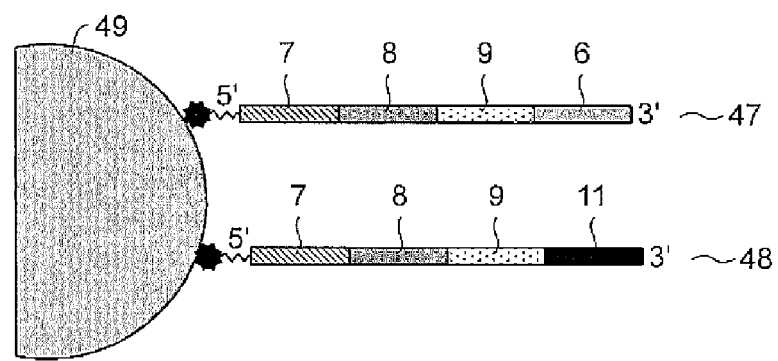

The first probe and the second probe used in this Example are immobilized to the carrier as shown in FIG. 8, and the carriers (nucleic acid probe immobilization carriers) having the nucleic acid probes immobilized are placed in a cell holding area in the substrate in configurations shown in FIGS. 8(a) and (b).

FIG. 8(a) shows a configuration in which first probes (47) and second probes (48) are immobilized on the same carrier (49) and the carriers (49) are placed in the cell holding area (1). FIG. 8(b) shows a configuration in which the first probes (47) and the second probes (48) are immobilized on different carriers, respectively. The first probes (47) are immobilized on carriers (50) and the second probes (48) are immobilized on carriers (51), and both the carriers are mixed and placed in the cell holding area (1).

The carriers used in this Example are a commercially available magnetic bead having a diameter of 1 µm and coated with streptavidin (Invitrogen), and the number of the nucleic acid probes that can be immobilized to one bead is about $10^5$. For example, when a cell holding area having a diameter of 30 µm and a depth of 70 µm is used, about $6 \times 10^4$ beads per area can be accommodated, and the total number of the nucleic acid probes is about $6 \times 10^9$. Since the reactions are conducted in the void space among the placed beads and the volume is estimated as fifth or sixth part or so of that of the cell holding area, the density of the nucleic acid probes in the reaction part is in the order of millimoles. That is, with the configuration of the Example, it is possible to allow the synthesized reaction product to react with the second probe very rapidly and efficiently, and the probability of loss of the reaction product through the re-capture is extremely low.

FIG. 8(c) shows a configuration of the nucleic acid probes on the carrier (49) shown in FIG. 8(a) and sequence configurations of the first probe (47) and the second probe (48) therein. The first probe (47) has a base sequence represented by SEQ ID No. 1 which is the same as that in the first probe (5) used in Example 1. The second probe (48) also has a base sequence represented by SEQ ID No. 2 which is the same as that in the second probe (10) in Example 1. The 5' end of each probe is modified with biotin for immobilization to a carrier.

In this Example, the second probe (48) may be installed under the cell holding area (1), for example, between the cell holding area (1) and the porous membrane (3) in a state of being encapsulated in agarose gel which dissolves at 80° C. In this case, by applying a heat treatment at 80° C. or higher before the reaction product capturing step or at the beginning of the step to dissolve the gel, the second probe (48) can be spread into the cell holding area.

In this Example, the magnetic bead of a diameter of 1 m coated with streptavidin (Invitrogen) as described above was used as the carrier. In the configuration of FIG. 8(a), the first probes (47) were immobilized at about $1 \times 10^{11}$ molecules/$10^7$ beads/µL, and the second probes (48) were immobilized at about $5 \times 10^{11}$ molecules/$10^7$ beads/µL, on a carrier (49). In the configuration of FIG. 8(b), the first probes (47) and the second probes (48) were immobilized at $5 \times 10^{11}$ molecules/$10^7$ beads/µL each on the respective carriers (50) and (51), and the carriers were mixed so as to exist at a ratio of 1:5. The immobilization of the nucleic acid probes on the carriers was performed according to a manual of magnetic beads. The carriers on which both the nucleic acid probes were immobilized and the mixed carriers in which the respective nucleic acid probes were immobilized on the respective different carriers were individually charged into an inkjet printer head, and 6 nL each of the beads on which a unique tag sequence for each cell holding area was immobilized were individually charged into the cell holding areas so that $3 \times 10^9$ probes per cell holding area were placed therein.

Next, a method for capturing cells using the gene analysis system of the Example will be described. First, 1000 or less cells were washed with 500 µL of 1×PBS and then suspended in 100 µL of 1×PBS cooled to 4° C. The cell solution was arranged in the areas of FIG. 1(d) in an array form. Concretely, an Anodisc having a pore size of 0.1 µm was laminated on a PDMS sheet of a thickness of 80 µm having 1000 through holes with an upper diameter of 5 µm and a lower diameter of 75 µm arranged. The carriers having the nucleic acid probes immobilized were charged in cell holding areas formed by lamination of the PDMS sheet and the Anodisc. The Anodisc in this embodiment has a role of holding the carriers unlike in the gene analysis system of Example 1. Since the PDMS sheet and the Anodisc have been subjected to a hydrophilic treatment, the solution can pass through the through holes. By allowing the cell solution prepared as described above to flow from the top toward the bottom of the substrate, cells moves along the solution flow to reach the top of the cell holding area. Since the opening diameter of the cell holding area in this Example is smaller than the diameter of a cell, the cell is captured thereon in a fixed state. Since the cell captured plays a role of a plug against the solution flow, the flow with cells that have not been captured yet moves toward the top of the cell holding areas that have not captured cells yet.

Subsequently, a cell captured on the substrate was lysed by an ordinary method using a cytolysis reagent, an obtained mRNA was captured by the first probe, and then a reaction product having a tag sequence introduced was obtained. The method and the reaction flow are the same as in Example 1 shown in FIG. 2 and FIG. 4. Hereinbelow, concrete reaction conditions will be described based on FIG. 4. Into the cell capturing substrate (18) formed of the aforementioned substrate having about 1000 cells captured, 100 µL of the cytolysis reagent (19) was added at a flow rate of 20 µL/minute and allowed to react at room temperature for 5 minutes to lyse the cell. While the solution is allowed to flow to lyse the cell, the mRNA moves to the cell holding area just under the cell, and therefore the mRNA is captured by the first probe present in the cell holding area. Instead of allowing the cell lysate to continuously flow, voltage may be applied to allow the nucleic acid to move toward the carrier. After that, a reaction product synthesizing primer (1 µM) formed of a random sequence of 7 bases was added, and then 50 µL of the reaction liquid (20) composed of the reverse transcriptase (200 U) and the reverse transcription reaction reagent was added at a flow rate of 500 nL/minute, and allowed to react in the reaction device (21) at room temperature for 10 minutes, at 37° C. for 10 minutes, and at 50° C. for 50 minutes. After that, 10 µL of the reaction liquid (22) composed of the RNase H (60 U) and the RNase H reaction reagent was added and allowed to react in the reaction device (23) at 37° C. for 15 minutes. Further, 10 µL of the reaction liquid (24) containing the DNA polymerase (5 U) and the DNA polymerase reaction reagent was added and allowed to react in the reaction device (25) at 98° C. for 10 seconds, at 40° C. for 1 minute, and at 68° C. for 1 minute, followed by cooling to 4° C. Through the above reactions, a cDNA having a sequence complementary to a base sequence of the mRNA (reaction product) was synthesized using the first probe as a primer, the obtained reaction product was captured by the second probe, and a DNA strand was synthesized by the DNA polymerase, whereby a reaction product having a tag sequence unique for each cell holding area added could be obtained. In the reaction steps in this Example, the configuration of FIG. 1(*d*) is used, but all the configurations shown in FIG. 1 may be used.

Next, an amplifying step (VI) was performed using a tag sequence-introduced product obtained in this Example as a template. The amplification method will be described below. After the tag sequence introducing step (V), a modification reaction for adding a poly-A sequence to the 3' end of the tag sequence-introduced product was performed. The reaction was performed by a method according to Example 2. After that, using 30 bases of poly-T sequence which is a complementary sequence of the modified nucleic acid sequence (poly-A sequence) as a reverse primer (represented by SEQ ID No. 7), and 15 bases from the 5' end of the common sequence (7) of the second probe as a forward primer (represented by SEQ ID No. 8), an amplification reaction was performed. Although this Example describes the case where the modification nucleic acid sequence to the tag sequence-introduced product is poly-A, a sequence other than poly-A may be used similarly as in Example 2. In this case, as a sequence of the reverse primer used in the amplification reaction, a complementary sequence of the modification nucleic acid sequence may be used.

When a sequence analysis of the amplified product obtained by the amplifying step is performed, it is possible to determine the specific gene sequence for each cell holding area or each group of cell holding areas on the device based on the information of the tag sequence contained in the amplified product. In addition, in the reaction steps of this Example, all or any of the mRNA degradation, the reaction product capturing step, and the tag sequence introducing step may be conducted at the same time.

Example 4

Figure 10:
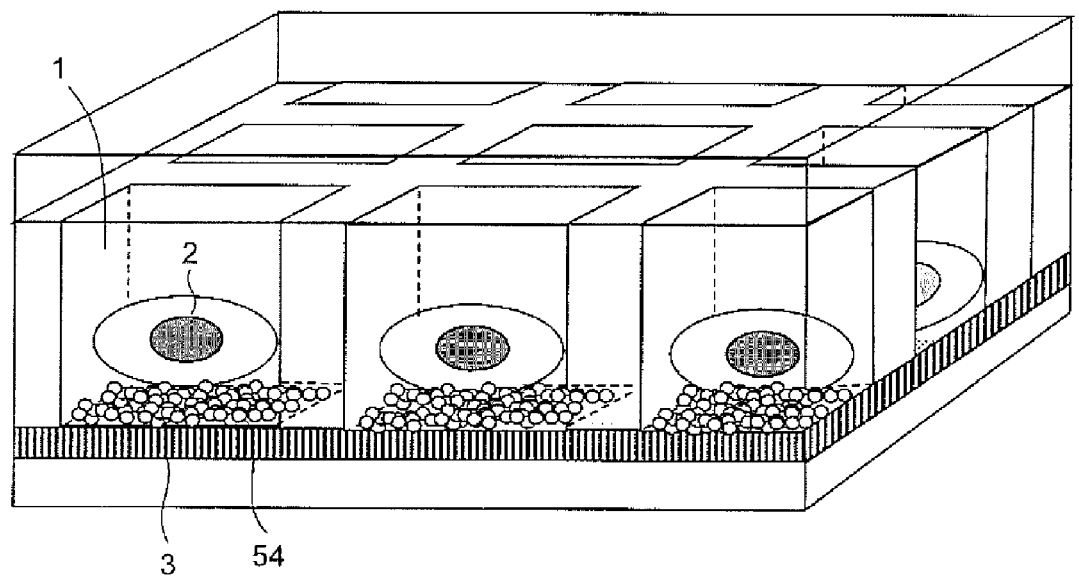
FIG. 10 is a diagram showing a substrate configuration, a nucleic acid probe configuration, and an immobilization mode of a nucleic acid probe in the gene analysis system used in Example 4. (a) shows a substrate configuration in a mode in which each cell is held in one cell holding area and probes are immobilized to carriers, and (b) and (c) show different immobilization modes of nucleic acid probes to a carrier.
Figure 10:
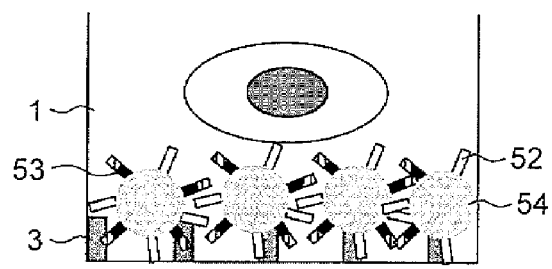
Figure 10:
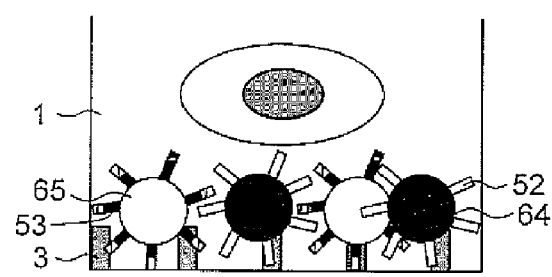

This Example describes a method, in which the substrate shown in FIG. 1(*e*) in which carriers having DNA probes immobilized are introduced in plural separated cell holding areas and a gene analysis system shown in FIGS. 9 and 10 in which first probes and second probes are placed in each of the cell holding areas are used. A single strand nucleic acid derived from a single cell captured by the first probe is used as a template to synthesize a complementary strand (first reaction product) from the first probe. Then, a reaction product (second reaction product) which is obtained from a reaction product synthesizing probe using the complementary strand as a template is modified, thereby capturing the reaction product again in the cell holding area, and the captured sequence derived from the reaction product is introduced into the second probe.

As shown in FIG. 9, in this Example, a gene expression system of a configuration in which a first probe (52) and a second probe (53) are immobilized on the same carrier (54) was used. A nucleic acid capturing sequence (55) in the sequence of the first probe (52) (represented by SEQ ID No. 9) is different in the base length from the nucleic acid capturing sequence (6) in the first probes represented by SEQ ID Nos. 1 and 5. The second probe is represented by SEQ ID No. 2, that is, has the same sequence as that in the embodiment of Examples 1 and 3. As the carrier (54) used in this Example, one having streptavidin immobilized is used and the 5' end of each probe is modified with biotin for immobilization onto the carrier. The reaction steps using the gene analysis system of this Example include: a cell holding step (I) in which the mRNA (12) which is a single strand nucleic acid is extracted from the cell (2) held in the cell holding area; a single strand nucleic acid capturing step (II) in which the mRNA (12) is captured by hybridization with a nucleic acid capturing sequence (55) of the first probe (52); a reaction product synthesizing step (III) in which using the captured mRNA (12) as a template, a first reaction product (56) is synthesized with the 3' end of the first probe (52) as a starting point, then the mRNA is degraded (16), and using the first reaction product (56) as a template, second reaction products (59) and (60) are synthesized with the 3' ends of the reaction product synthesizing primers (57) and (58) as starting points; a reaction product capturing step (IV) in which the 3' ends of the second reaction products are modified with biotin and then heated to thereby separate biotin-modified reaction products (61) and (62) from the first reaction product (56), and the biotin-modified reaction products (61) and (62) are coupled to streptavidin on the carrier (54); and a tag sequence introducing step (V) in which the reaction product capturing sequence (11) of the second probe (53) is hybridized with a part of the biotin-modified reaction product (61) and a DNA strand (tag sequence-introduced product (63)) is synthesized using the biotin-modified reaction product (61) as a template, thereby introducing a tag sequence into a sequence derived from the reaction product. When a DNA is captured as a target nucleic acid in the single strand nucleic acid capturing step (II) of this Example, the step of degrading the RNA is unnecessary. Furthermore, all or any of the reaction product capturing step (IV) and the tag sequence introducing step (V) may be conducted at the same time.

Using the tag sequence-introduced product (63) obtained in the tag sequence introducing step as a template, and using the common sequence (7) as a forward primer, and the random sequence represented by SEQ ID No. 3 used in Example 1 as a reverse primer, the amplifying step (VI) may be performed. Thus, it is possible to perform a sequence analysis of the obtained amplified product while determining a specific gene sequence for each cell holding area or each group of cell holding areas on the device based on the information of the tag sequence contained therein. Incidentally, although a random sequence is used as a reverse primer in this Example, when the reaction product synthesizing primer with a common sequence (SEQ ID No. 4) is used, a complementary strand of the common sequence may be used as a reverse primer, and when the 3' end of the tag sequence-introduced product is subjected to a nucleic acid modification, a complementary strand of the nucleic acid-modified sequence may be used as a reverse primer, as shown in Examples 2 and 3.

Next, the configuration of the substrate used in this Example in which carriers having DNA probes immobilized are introduced in plural separated areas is shown in FIG. 10(*a*), and configurations of immobilizing the probes are shown in FIGS. 10(*b*) and (*c*).

First, as shown in FIG. 10(*a*), the carriers (54) on which DNA probes were immobilized are added in the cell holding area (1). A cell is held in the area, and an extracted nucleic acid is hybridized to the first probe (52) present on the carrier. In this time, the porous membrane (3) plays a roll of holding the carriers (54).

Next, the configuration of immobilizing probes will be described. FIG. 10(b) shows a configuration in which the first probes (52) and the second probes (53) are immobilized on the surface of the same carrier (54). FIG. 10(c) shows a configuration in which the first probes (52) are immobilized on carriers (64) and the second probes (53) are immobilized on carriers (65), and both the carriers are mixed.

In this Example, the same magnetic bead (Invitrogen) as in Example 3 which had a diameter of 1 µm and was coated with streptavidin was used as the carrier. The amounts of the nucleic acid probes immobilized on the carriers in the configurations of FIGS. 10(b) and (c) are the same as in Example 2. The carriers or the mixed carriers having the nucleic acid probes immobilized were individually charged in an inkjet printer head, and 6 nL each of the beads on which different sequences were immobilized were individually charged into the cell holding areas (1) shown in FIG. 10(a). Incidentally, as shown in FIG. 1(e), like in Examples 1 and 2, a method in which the first and the second probes are directly immobilized onto the porous membrane (3) may be used. Although the reaction steps use the substrate of the configuration of FIG. 1(e), all the configurations shown in FIG. 1 may be used.

Next, a method for capturing cells using the gene analysis system of this Example will be described. First, 1000 or less cells were washed with 500 µL of 1×PBS in a manner that did not damage the cells, and then the solution was removed, and 500 µL of 1×PBS cooled to 4° C. was added. The cell solution was arranged in the areas of FIG. 10(a) in an array form. Concretely, a PDMS sheet of a 0.1 mm thickness in which 1000 cell holding areas having a diameter of 10 µm were arranged was laminated with an Anodisc having a pore size of 0.1 µm (GE Healthcare). By allowing the cell solution to flow from the top toward the bottom of the substrate in the gene analysis system of this Example, the cells were held in the respective cell holding areas. In this manner, approximately 80% of the cells could be captured one-by-one to the respective cell holding areas.

Subsequently, the cells held on the substrate were lysed by an ordinary method using a cytolysis reagent, and after the obtained mRNA was captured by the first probe, a complementary strand was synthesized with the first probe as a starting point, and the RNA was degraded by RNase H. After that, using the complementary strand as a template, a reaction product was synthesized with a reaction product synthesizing primer as a starting point, and the 3' end of the reaction product was modified with biotin to thereby capture the reaction product in the cell holding area. After that, using the captured reaction product as a template, a DNA strand was synthesized from the second probe, thereby introducing a tag sequence. In this Example, as shown in FIG. 9, the biotin modification was performed by adding a biotin-labeled dUTP to the 3' end of the reaction product with TdT. After that, the complementary strand and the reaction product were separated due to thermal denaturation, and the biotinated modified reaction product was captured by biotin-streptavidin binding with the carrier coated with streptavidin in the cell holding area. The affinity of streptavidin to biotin is very rigid with the dissociation constant of $10^{-15}$ M. For this reason, the biotin-modified reaction product can be immediately coupled to the carrier surface after thermal denaturation, and by the configuration of this Example, the loss by re-capture of the reaction product can be reduced to substantially 0%. After being captured, the reaction product was hybridized with the second probe via a complementary sequence of the biotin-modified reaction product, and a complementary strand of the reaction product was synthesized by a DNA polymerase using the second probe as a primer. In this Example, SuperScript III (Invitrogen) was used as a reverse transcriptase, RNase H (Invitrogen) was used as an enzyme for removing the RNA, TdT (Thermoscientific) was used as a biotin modification enzyme, and Platinum Taq Hi Fidelity DNA polymerase (Invitrogen) was used as a DNA polymerase. The compositions of the cytolysis reagent, the reverse transcription reaction reagent, and the RNase H reagent are the same as those shown in Tables 1 to 3. The compositions of the biotin modification enzyme reaction reagent and the DNA polymerase reaction reagent are shown in Tables 8 and 9.

TABLE 8

Composition of biotin modification enzyme reaction reagent (all from Thermoscientific)

| Reagent | Charge amount |
| --- | --- |
| ×5 TdT Reaction buffer | ×1 |
| 5 uM Biotin-11-UTP | 0.5 uM |

TABLE 9

Composition of DNA polymerase reaction reagent (all from Invitrogen)

| Reagent | Charge amount |
| --- | --- |
| ×10 Buffer | ×1 |
| 2.5 mM dNTPs | 0.25 mM |
| 50 mM MgSO$_4$ | 2.0 mM |

Figure 11:
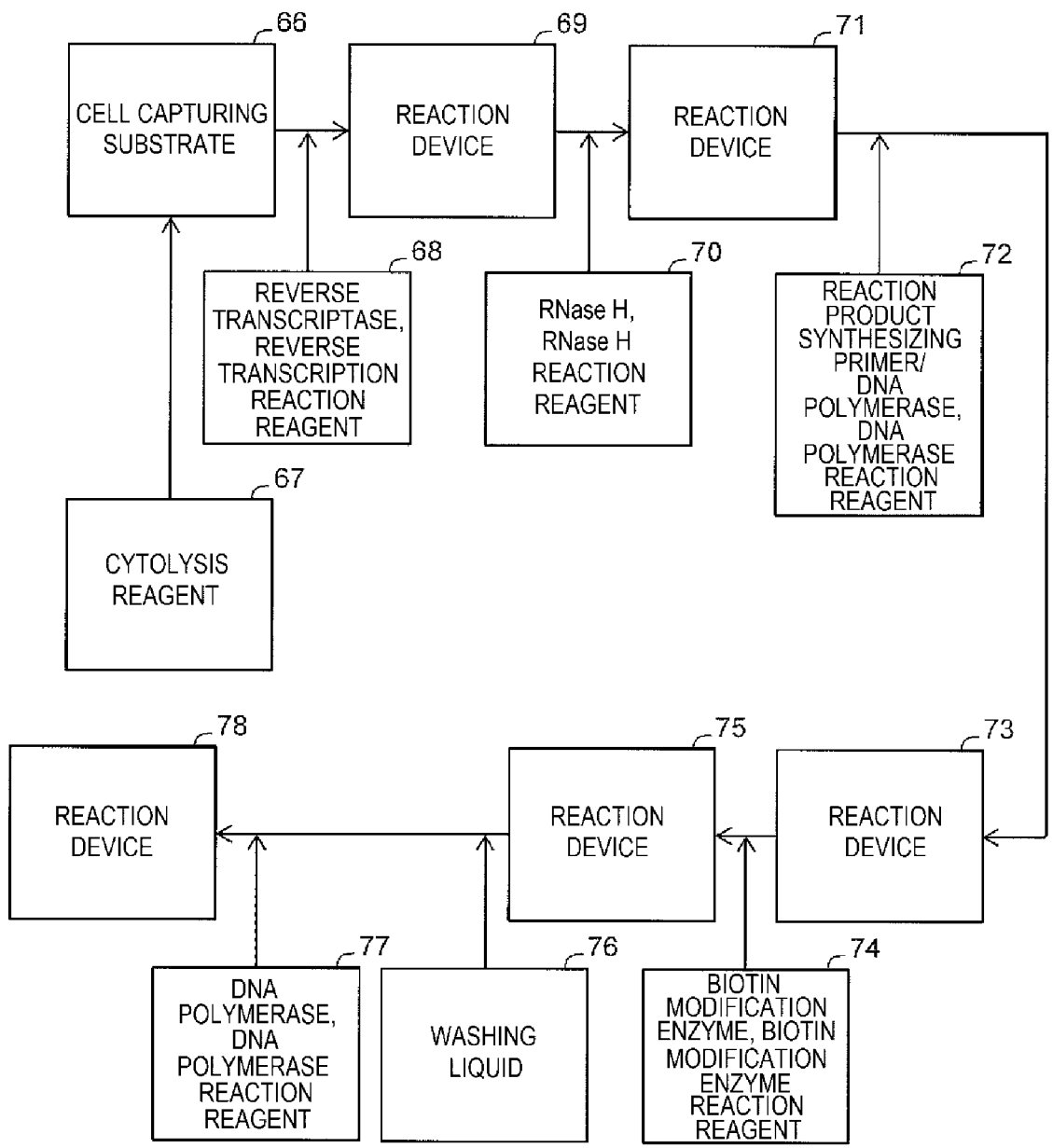
FIG. 11 is a diagram showing one embodiment of the reaction flow in the present invention.

FIG. 11 shows the reaction flow of this Example, and concrete reaction conditions will be described below. To a cell capturing substrate (66) formed of the aforementioned substrate in which about 1000 cells were captured, 100 µL of a cytolysis reagent (67) was added at a flow rate of 20 µL/minute, and allowed to react at room temperature for 5 minutes to lyse the cells. In the same manner as in Example 3, the solution was allowed to flow to lyse the cells and at the same time, an mRNA moves into a cell holding area just under the cell, and the mRNA is captured by the first probe present in the cell holding area. In this time, instead of allowing the cell lysate to continuously flow, voltage may be applied to allow the nucleic acid to move toward the carrier. After that, 50 µL of a reaction liquid (68) composed of the reverse transcriptase (200 U) and the reverse transcription reaction reagent was added at a flow rate of 500 nL/minute, and allowed to react in a reaction device (69) at 50° C. for 50 minutes. After that, 10 µL of a reaction liquid (70) containing the RNase H (60 U) and the RNase H reaction reagent was added and allowed to react in a reaction device (71) at 37° C. for 15 minutes. After the reaction, the reaction product synthesizing primer (1 µM), the DNA polymerase, and 12 µL of the DNA polymerase reaction reagent (72) were added and allowed to react in a reaction device (73) at 98° C. for 10 seconds, at 40° C. for 60 seconds, and at 68° C. for 180 seconds to synthesize a reaction product. After that, 11 µL of a reaction liquid (74) composed of a biotin modification enzyme (2 U) and a biotin modification enzyme reaction reagent was added and allowed to react in a reaction device (75) at 37° C. for 30 minutes, and then effect thermal denaturation at 80° C. for 180 seconds, thereby capturing the reaction product modified with biotin in the cell capturing area. After the reaction, 50 µL of a washing liquid (76) composed of 0.1% Tween 20/10 mM Tris (pH 8.0) was added to the gene analysis system at a flow rate of 20 μL/minute to wash the reaction product, and 10 μL of a reaction liquid (77) containing the DNA polymerase and the DNA polymerase reaction reagent was added and allowed to react in a reaction device (78) at 98° C. for 10 seconds, at 43° C. for 60 seconds, and at 68° C. for 180 seconds to synthesize a complementary strand of the reaction product with the second probe coupled thereto. Through the above reactions, a cDNA which was a complementary strand of the mRNA was synthesized using the first probe as a primer, and after the degradation of the RNA, a reaction product was synthesized using the complementary strand as a template. After that, the reaction product was modified with biotin, and a complementary strand of the reaction product was synthesized from the second probe, whereby a sequence derived from the reaction product having a tag sequence for each cell holding area added could be obtained. In this Example, the amplifying step (VI) may be performed by the method in Examples 1 to 3. In this case, in each step, the reaction may be conducted using a reagent and primer required.

INDUSTRIAL APPLICABILITY

According to the present invention, it is possible to determine, quantify, and identify a sequence of a gene derived from a biological molecule for a large number of cultured cells, a large number of immune cells or (blood) cancer cells, and the like, and it is possible to measure a number of cells in a certain state present in a living body. This makes it possible to early diagnose a cancer and the like and to measure heterogeneity of iPS cells.

1, 26, 27: Cell holding area
2: Cell
3: Porous membrane
4, 49, 50, 51, 54, 64, 65: Carrier
5, 28, 47, 52: First probe
6, 55: Nucleic acid capturing sequence
7, 30: Common sequence
8: Nucleic acid amplification correcting sequence
9, 29: Tag sequence
10, 48, 53: Second probe
11: Reaction product capturing sequence
12: Single strand nucleic acid (mRNA)
13, 31, 57, 58: Reaction product synthesizing primer
14, 32: Reaction product
15: Complementary sequence of reaction product capturing sequence
16: mRNA degradation product
17, 35, 63: Tag sequence-introduced product
18, 37, 66: Cell capturing substrate
19, 38, 67: Cytolysis reagent
20, 39: Reaction product synthesizing primer/reverse transcriptase and reverse transcriptase reaction reagent
21, 23, 25, 40, 42, 44, 46, 69, 71, 73, 75, 78: Reaction device
22, 67, 43, 70: RNase H, RNase H reaction reagent
24, 45, 77: DNA polymerase, and DNA polymerase reaction reagent
33: Nucleic acid modification sequence
34: Modified reaction product
36: Complementary sequence of nucleic acid modification sequence
41: Modification enzyme, and modification enzyme reaction reagent
56: First reaction product
59, 60: Second reaction product
61, 62: Biotin-modified reaction product
68: Reverse transcriptase and reverse transcription reaction reagent
72: Reaction product synthesizing primer, DNA polymerase, and DNA polymerase reaction reagent
74: Biotin modification enzyme, and biotin modification enzyme reaction reagent
76: Washing liquid

SEQUENCE LISTING FREE TEXT

SEQ ID No. 1: description of artificial sequence: first probe used in Examples 1, 2, 3, and 4 of the present invention
SEQ ID No. 2: description of artificial sequence: second probe used in Examples 1, 3, and 4 of the present invention
SEQ ID No. 3: description of artificial sequence: forward primer for amplification used in Example 1 of the present invention
SEQ ID No. 4: description of artificial sequence: reverse primer for amplification used in Examples 1 and 4 of the present invention
SEQ ID No. 5: first probe used in Example 2 of the present invention
SEQ ID No. 6: description of artificial sequence: reaction product synthesizing primer used in Example 2 of the present invention
SEQ ID No. 7: description of artificial sequence: reverse primer for amplification used in Example 3 of the present invention
SEQ ID No. 8: description of artificial sequence: forward primer for amplification used in Example 3 of the present invention
SEQ ID No. 9: first probe used in Example 4 of the present invention All the publications, patent documents, and patent applications cited in the Description are entirely incorporated herein by reference.

The invention claimed is:

1. A gene analysis system, comprising:
a substrate including a cell holding area configured to hold one cell arranged on the substrate;
a first probe that is placed on an inner surface of the cell holding area below the one cell, and has a nucleic acid capturing sequence;
a second probe that is placed on the inner surface of the same cell holding area below the one cell, and has a tag sequence which identifies the cell holding area and a reaction product capturing sequence,
wherein the nucleic acid capturing sequence of the first probe is configured to hybridize with a single strand nucleic acid extracted from the cell,
wherein the reaction product capturing sequence of the second probe is configured to hybridize with a reaction product which is synthesized from the single strand nucleic acid, the reaction product having a complementary sequence to the single strand nucleic acid,
wherein the second probe is further configured to hybridize with the reaction product and synthesize a tag sequence-introduced product having a complementary sequence to the reaction product, and which includes the tag sequence of the second probe which identifies the cell holding area,
wherein the reaction product capturing sequence of the second probe is different than the nucleic acid capturing sequence of the first probe, and
wherein the first probe comprises SEQ ID No. 1.

2. The system according to claim 1, wherein the reaction product capturing sequence of the second probe is different than the nucleic acid capturing sequence of the first probe and wherein the second probe has the tag sequence which uniquely identifies the cell holding area in the substrate.

3. The system according to claim 1, wherein the second probe further has at least one of a common sequence and a nucleic acid amplification correcting sequence.

4. The system according to claim 1, wherein the first probe and the second probe are immobilized on a same carrier placed on the inner surface of the cell holding area.

5. The system according to claim 1, wherein the first probe and the second probe are immobilized on the inner surface of cell holding area via a joint molecule.

6. The system according to claim 1, wherein the first probe and the second probe are immobilized on different carriers placed on the inner surface of the cell holding area.

7. The system according to claim 1, wherein the second probe comprises SEQ ID No. 2.

8. A gene analysis system, comprising:
a substrate including a cell holding area configured to hold one cell arranged on the substrate;
a first probe that is placed on an inner surface of the cell holding area below the one cell, and has a nucleic acid capturing sequence;
a second probe that is placed on the inner surface of the same cell holding area below the one cell, and has a tag sequence which identifies the cell holding area and a reaction product capturing sequence,
wherein the nucleic acid capturing sequence of the first probe is configured to hybridize with a single strand nucleic acid extracted from the cell,
wherein the reaction product capturing sequence of the second probe is configured to hybridize with a reaction product which is synthesized from the single strand nucleic acid, the reaction product having a complementary sequence to the single strand nucleic acid,
wherein the second probe is further configured to hybridize with the reaction product and synthesize a tag sequence-introduced product having a complementary sequence to the reaction product, and which includes the tag sequence of the second probe which identifies the cell holding area,
wherein the reaction product capturing sequence of the second probe is different than the nucleic acid capturing sequence of the first probe, and
wherein the first probe comprises SEQ ID No. 5, and the second probe comprises SEQ ID No. 2.

9. A gene analysis system, comprising:
a substrate including a cell holding area configured to hold one cell arranged on the substrate;
a first probe that is placed on an inner surface of the cell holding area below the one cell, and has a nucleic acid capturing sequence;
a second probe that is placed on the inner surface of the same cell holding area below the one cell, and has a tag sequence which identifies the cell holding area and a reaction product capturing sequence,
wherein the nucleic acid capturing sequence of the first probe is configured to hybridize with a single strand nucleic acid extracted from the cell,
wherein the reaction product capturing sequence of the second probe is configured to hybridize with a second reaction product which is synthesized from a first reaction product having a complementary sequence to the single strand nucleic acid, the second reaction product having a complementary sequence to the first reaction product,
wherein the second probe is further configured to hybridize with the second reaction product and synthesize a tag sequence-introduced product having a complementary sequence to the second reaction product and the tag sequence of the second probe which identifies the cell holding area,
wherein the reaction product capturing sequence of the second probe is different than the nucleic acid capturing sequence of the first probe, and
wherein the nucleic acid capturing sequence of the first probe comprises SEQ ID No. 9.

10. The system according to claim 9, wherein the reaction product capturing sequence of the second probe is different than the nucleic acid capturing sequence of the first probe and wherein the second probe has the tag sequence which uniquely identifies the cell holding area in the substrate.

11. The system according to claim 9, wherein the second probe further has at least one of a common sequence and a nucleic acid amplification correcting sequence.

12. The system according to claim 9, wherein the first probe and the second probe are immobilized on a same carrier placed on the inner surface of the cell holding area.

13. The system according to claim 9, wherein the first probe and the second probe are immobilized on the inner surface of cell holding area via a joint molecule.

14. The system according to claim 9, wherein the first probe and the second probe are immobilized on different carriers placed on the inner surface of the cell holding area.

15. The system according to claim 9, wherein the second probe comprises SEQ ID No. 2.

16. A gene analysis system, comprising:
a substrate including a cell holding area configured to hold one cell arranged on the substrate;
a first probe that is placed on an inner surface of the cell holding area below the one cell, and has a nucleic acid capturing sequence;
a second probe that is placed on the inner surface of the same cell holding area below the one cell, and has a tag sequence which identifies the cell holding area and a reaction product capturing sequence,
wherein the nucleic acid capturing sequence of the first probe is configured to hybridize with a single strand nucleic acid extracted from the cell,
wherein the reaction product capturing sequence of the second probe is configured to hybridize with a second reaction product which is synthesized from a first reaction product having a complementary sequence to the single strand nucleic acid, the second reaction product having a complementary sequence to the first reaction product,
wherein the second probe is further configured to hybridize with the second reaction product and synthesize a tag sequence-introduced product having a complementary sequence to the second reaction product and the tag sequence of the second probe which identifies the cell holding area,
wherein the reaction product capturing sequence of the second probe is different than the nucleic acid capturing sequence of the first probe, and
wherein the nucleic acid capturing sequence of the first probe comprises SEQ ID No. 9, and the second probe comprises SEQ ID No. 2.

* * * * *